(12) United States Patent
Radhakrishnan et al.

(10) Patent No.: US 9,308,263 B2
(45) Date of Patent: Apr. 12, 2016

(54) PHARMACEUTICAL COMPOSITIONS AND USES THEREOF

(71) Applicant: Seachaid Pharmaceuticals, Inc., Durham, NC (US)

(72) Inventors: Balasingam Radhakrishnan, Chapel Hill, NC (US); Anuradha Vaidya, Raleigh, NC (US); Navdeep Balkrishna Malkar, Cary, NC (US); Karen Polowy, Raleigh, NC (US); Kenneth Duke James, Jr., Mebane, NC (US)

(73) Assignee: Seachaid Pharmaceuticals, Inc., Mebane, NC (US)

( * ) Notice: Subject to any disclaimer, the term of this patent is extended or adjusted under 35 U.S.C. 154(b) by 0 days.

(21) Appl. No.: 14/352,966

(22) PCT Filed: Oct. 19, 2012

(86) PCT No.: PCT/US2012/061125
§ 371 (c)(1),
(2) Date: Apr. 18, 2014

(87) PCT Pub. No.: WO2013/059664
PCT Pub. Date: Apr. 25, 2013

(65) Prior Publication Data
US 2014/0329793 A1 Nov. 6, 2014

Related U.S. Application Data

(60) Provisional application No. 61/549,882, filed on Oct. 21, 2011.

(51) Int. Cl.
| | | |
|---|---|---|
| *A61K 47/14* | (2006.01) | |
| *A61K 45/06* | (2006.01) | |
| *A61K 31/397* | (2006.01) | |
| *A61K 47/26* | (2006.01) | |
| *A61K 9/107* | (2006.01) | |
| *A61K 9/48* | (2006.01) | |
| *A61K 38/12* | (2006.01) | |
| *A61K 31/43* | (2006.01) | |
| *A61K 31/431* | (2006.01) | |
| *A61K 31/546* | (2006.01) | |

(52) U.S. Cl.
CPC ............... *A61K 47/14* (2013.01); *A61K 9/107* (2013.01); *A61K 9/4858* (2013.01); *A61K 31/397* (2013.01); *A61K 31/43* (2013.01); *A61K 31/431* (2013.01); *A61K 31/546* (2013.01); *A61K 38/12* (2013.01); *A61K 45/06* (2013.01); *A61K 47/26* (2013.01)

(58) Field of Classification Search
USPC .................... 514/192, 785, 777, 202
See application file for complete search history.

(56) References Cited

U.S. PATENT DOCUMENTS

| | | | |
|---|---|---|---|
| 4,537,772 A | 8/1985 | Alexander et al. | |
| 4,788,221 A | 11/1988 | Kagatani et al. | |
| 7,348,166 B2 | 3/2008 | Nakajima | |
| 2003/0064097 A1 | 4/2003 | Patel et al. | |
| 2003/0180352 A1* | 9/2003 | Patel et al. ................... | 424/465 |
| 2004/0038866 A1 | 2/2004 | Soltero et al. | |
| 2004/0091452 A1 | 5/2004 | Ekwuribe et al. | |
| 2006/0008850 A1 | 1/2006 | Riggs-Sauthier et al. | |
| 2006/0258743 A1 | 11/2006 | Nakajima | |
| 2008/0125380 A1 | 5/2008 | Webb et al. | |
| 2008/0145411 A1 | 6/2008 | Shinagawa et al. | |
| 2008/0213366 A1 | 9/2008 | Gowan, Jr. et al. | |
| 2009/0182052 A1* | 7/2009 | Djordjevic et al. .......... | 514/569 |

FOREIGN PATENT DOCUMENTS

| | | | |
|---|---|---|---|
| WO | WO-02/098232 A1 | 12/2002 | |
| WO | WO-02/098446 A1 | 12/2002 | |
| WO | WO-02/098451 A1 | 12/2002 | |
| WO | WO-02/098452 A1 | 12/2002 | |
| WO | WO-2004/002458 A1 | 1/2004 | |
| WO | WO-2005/004792 A2 | 1/2005 | |
| WO | WO-2005/030142 A2 | 4/2005 | |
| WO | WO-2009/131995 A1 | 10/2009 | |
| WO | WO-2010032218 A2 | 3/2010 | |
| WO | WO 2011/076743 | * | 6/2011 |
| WO | WO-2014/176501 A1 | 10/2014 | |

OTHER PUBLICATIONS

Jauregui et al. (J. of Antimicrobial Chemotherapy (1993), 32 suppl. B, 141-149).*
Fernandez et al. "Comparative study on digestive lipase activities on the self emulsifying excipient Labrasol, medium chain glycerides and PEG esters," Biochim Biophys Acta. 1771(5):633-40 (2007).
Hu et al. "Diethyl ether fraction of Labrasol having a stronger absorption enhancing effect on gentamicin than Labrasol itself" Int J Pharm. 234(1-2):223-35 (2002).
Zaslaysky et al. "Action of surface-active substances on biological membranes. II. Hemolytic activity of nonionic surfactants," Biochim Biophys Acta. 507(1):1-7 (1978).
International Preliminary Report on Patentability for International Patent Application No. PCT/US2012/061125, dated Apr. 22, 2014 (14 pages).
Extended European Search Report for European Patent Application No. 12841549.4, dated Jul. 9, 2015 (8 pages).
Sutton et al., "Enhanced bioavailability of cefoxitin using palmitoyl L-carnitine. I. Enhancer activity in different intestinal regions." Pharm Res. 9(2): 191-4 (1992).
Sutton et al., "Enhanced bioavailability of cefoxitin using palmitoylcarnitine. II. Use of directly compressed tablet formulations in the rat and dog." Pharm Res. 10(10):1516-20 (1993).

* cited by examiner

*Primary Examiner* — Shirley V Gembeh
(74) *Attorney, Agent, or Firm* — Clark & Elbing LLP

(57) ABSTRACT

The invention features pharmaceutical compositions including (i) a drug, and (ii) a PEG fatty acid ester or PPG fatty acid ester in an amount sufficient to increase the oral bioavailability of the drug.

43 Claims, No Drawings

PHARMACEUTICAL COMPOSITIONS AND USES THEREOF

CROSS-REFERENCE TO RELATED APPLICATIONS

This application is the U.S. National Phase of International Application No. PCT/US2012/061125, filed Oct. 19, 2012, which claims benefit of the U.S. Provisional Application No. 61/549,882, filed Oct. 21, 2011, and incorporated herein by reference.

BACKGROUND OF THE INVENTION

This invention relates to the field of formulations for orally administered drugs.

To be pharmaceutically effective, an orally administered drug must be absorbed into the bloodstream through epithelial cells lining the gastrointestinal tract. Many drug candidates cannot be orally administered because of poor absorptive characteristics. Hence, the development of reagents suitable for medicinal use that improve oral bioavailability when co-administered with pharmaceuticals is a primary focus in drug development and medicinal chemistry.

A number of potent antibiotics and antibiotic prodrugs have inadequate oral bioavailability on their own. For this reason, such antibiotics are traditionally administered intravenously to treat serious infections. However, intravenous administration is an invasive procedure that is potentially detrimental to the subject (side effects include IV-line phlebitis and sepsis), inconvenient, and costly. Thus, there is a need to develop formulations that enhance the oral bioavailability of antibiotics so as to increase the number of oral antibiotics available to subjects.

SUMMARY OF THE INVENTION

We have discovered oral dosage formulations for increasing the oral bioavailability of drugs, including cephalosporin and carbapenem antibiotics. The formulations include a PEG fatty acid monoester, a PEG fatty acid diester, a PPG fatty acid monoester, a PPG fatty acid diester, or a mixture thereof.

In a first aspect, the invention features a pharmaceutical composition in oral dosage form including (a) a drug; and (b) an additive including a PEG fatty acid ester or PPG fatty acid ester, wherein the additive is present in an amount sufficient to increase the oral bioavailability of the drug, and wherein the pharmaceutical composition is (i) substantially free of monoglycerides; (ii) substantially free of diglycerides; (iii) substantially free of triglycerides; (iv) substantially free of free polyethylene glycol; (v) substantially free of free polypropylene glycol; (vi) substantially free of fatty acid; (vii) substantially free of glycerol; (viii) includes a substantially pure PEG fatty acid ester; (ix) includes a substantially pure PEG fatty acid monoester; (x) includes a substantially pure PEG fatty acid diester; (xi) includes a substantially monodisperse PEG fatty acid ester; (xii) includes a substantially pure PPG fatty acid ester; (xiii) includes a substantially pure PPG fatty acid monoester; (xiv) includes a substantially pure PPG fatty acid diester; or (xv) includes a substantially monodisperse PPG fatty acid ester. In certain embodiments, the pharmaceutical composition is a unit dosage form including from 250 milligrams to 5.0 grams of drug, or a pharmaceutically acceptable salt thereof (e.g., from 250 mg to 500 mg, 400 mg to 750 mg, 600 mg to 1.5 g, 1.0 g to 2.5 g, 1.5 g to 3.0 g, or 2.5 g to 5.0 g). The unit dosage form can be, for example, a reconstitutable dosage form (e.g., an effervescent tablet or a sprinkle), a hard gel capsule, or a soft gel capsule. In particular embodiments the pharmaceutical composition includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PEG fatty acid diester. In other embodiments the ratio by weight of the PEG fatty acid diester to the drug is greater than 1:1, 2:1, 2.5:1, 3.0:1, or 3.5:1 (e.g., from 1:1 to 20:1, from 2:1 to 20:1, from 2.5:1 to 20:1, from 3:1 to 20:1, from 3:1 to 10:1, or from 4:1 to 20:1). The PEG fatty acid diester can, for example, be the dodecanoate diester, the decanoate diester, or the octanoate diester of a polyethylene glycol having from 1 to 20 PEG units (e.g., from 2 to 12 PEG units, from 4 to 10 PEG units, or from 6 to 9 PEG units). The PEG fatty acid diester can be formed, for example, from a polyethylene glycol mixture having an average chain length of from 8 to 9 PEG units in length. In still other embodiments the pharmaceutical composition includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PEG fatty acid monoester. In other embodiments the ratio by weight of the PEG fatty acid monoester to the drug is greater than 1:1, 2:1, 2.5:1, 3.0:1, or 3.5:1 (e.g., from 1:1 to 20:1, from 2:1 to 20:1, from 2.5:1 to 20:1, from 3:1 to 20:1, from 3:1 to 10:1, or from 4:1 to 20:1). The PEG fatty acid monoester can be, for example, the dodecanoate monoester, the decanoate monoester, or the octanoate monoester of a polyethylene glycol having from 1 to 20 PEG units (e.g., from 1 to 12 PEG units, from 2 to 10 PEG units, from 4 to 10 PEG units, or from 6 to 9 PEG units). The PEG fatty acid monoester can be, for example, formed from a polyethylene glycol mixture having an average chain length of from 8 to 9 PEG units in length. In still other embodiments the pharmaceutical composition includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PPG fatty acid diester. In other embodiments the ratio by weight of the PPG fatty acid diester to the drug is greater than 1:1, 2:1, 2.5:1, 3.0:1, or 3.5:1 (e.g., from 1:1 to 20:1, from 2:1 to 20:1, from 2.5:1 to 20:1, from 3:1 to 20:1, from 3:1 to 10:1, or from 4:1 to 20:1). The PPG fatty acid diester can be, for example, the dodecanoate diester, the decanoate diester, or the octanoate diester of a polypropylene glycol having from 1 to 20 PPG units (e.g., from 1 to 12 PPG units, 2 to 10 PPG units, from 4 to 10 PPG units, or from 6 to 9 PPG units). The PPG fatty acid diester can be formed from a polypropylene glycol mixture having an average chain length of from 8 to 9 PPG units in length. In still other embodiments the pharmaceutical composition includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PPG fatty acid monoester. In other embodiments the ratio by weight of the PPG fatty acid monoester to the drug is greater than 1:1, 2:1, 2.5:1, 3.0:1, or 3.5:1 (e.g., from 1:1 to 20:1, from 2:1 to 20:1, from 2.5:1 to 20:1, from 3:1 to 20:1, from 3:1 to 10:1, or from 4:1 to 20:1). The PPG fatty acid monoester can be, for example, the dodecanoate monoester, the decanoate monoester, or the octanoate monoester of a polypropylene glycol having from 1 to 20 PPG units (e.g., from 1 to 12 PPG units, from 2 to 10 PPG units, from 4 to 10 PPG units, or from 6 to 9 PPG units). The PPG fatty acid monoester can be formed, for example, from a polypropylene glycol mixture having an average chain length of from 8 to 9 PPG units in length.

In a related aspect, the invention features a reconstitutable pharmaceutical composition including from 0.5% to 20%

(w/w) (e.g., from 0.5% to 2%, 1.5% to 10%, 2.5% to 12%, or from 7.5% to 20% (w/w)) of a drug; and from 40% to 80% (w/w) (e.g., from 40% to 75%, 55% to 80%, or from 60% to 80% (w/w)) an additive including a PEG fatty acid ester or PPG fatty acid ester, wherein the additive is present in an amount sufficient to increase the oral bioavailability of the drug, and wherein the pharmaceutical composition is (i) substantially free of monoglycerides; (ii) substantially free of diglycerides; (iii) substantially free of triglycerides; (iv) substantially free of free polyethylene glycol; (v) substantially free of free polypropylene glycol; (vi) substantially free of fatty acid; (vii) substantially free of glycerol; (viii) includes a substantially pure PEG fatty acid ester; (ix) includes a substantially pure PEG fatty acid monoester; (x) includes a substantially pure PEG fatty acid diester; (xi) includes a substantially monodisperse PEG fatty acid ester; (xii) includes a substantially pure PPG fatty acid ester; (xiii) includes a substantially pure PPG fatty acid monoester; (xiv) includes a substantially pure PPG fatty acid diester; or (xv) includes a substantially monodisperse PPG fatty acid ester. In particular embodiments the reconstitutable pharmaceutical composition includes a substantially pure PEG fatty acid diester. In other embodiments the ratio by weight of the PEG fatty acid diester to the drug is greater than 1:1, 2:1, 2.5:1, 3.0:1, or 3.5:1 (e.g., from 1:1 to 20:1, from 2:1 to 20:1, from 2.5:1 to 20:1, from 3:1 to 20:1, from 3:1 to 10:1, or from 4:1 to 20:1). The PEG fatty acid diester can be, for example, the dodecanoate diester, the decanoate diester, or the octanoate diester of a polyethylene glycol having from 1 to 20 PEG units (e.g., from 1 to 12 PEG units, from 2 to 10 PEG units, from 4 to 10 PEG units, or from 6 to 9 PEG units). The PEG fatty acid diester can be formed, for example, from a polyethylene glycol mixture having an average chain length of from 8 to 9 PEG units in length. In still other embodiments the reconstitutable pharmaceutical composition includes a substantially pure PEG fatty acid monoester. In other embodiments the ratio by weight of the PEG fatty acid monoester to the drug is greater than 1:1, 2:1, 2.5:1, 3.0:1, or 3.5:1 (e.g., from 1:1 to 20:1, from 2:1 to 20:1, from 2.5:1 to 20:1, from 3:1 to 20:1, from 3:1 to 10:1, or from 4:1 to 20:1). The PEG fatty acid monoester can be, for example, the dodecanoate monoester, the decanoate monoester, or the octanoate monoester of a polyethylene glycol having from 1 to 20 PEG units (e.g., from 1 to 12 PEG units, from 2 to 10 PEG units, from 4 to 10 PEG units, or from 6 to 9 PEG units). The PEG fatty acid monoester can be formed, for example, from a polyethylene glycol mixture having an average chain length of from 8 to 9 PEG units in length. In still other embodiments the reconstitutable pharmaceutical composition includes a substantially pure PPG fatty acid diester. In other embodiments the ratio by weight of the PPG fatty acid diester to the drug is greater than 1:1, 2:1, 2.5:1, 3.0:1, or 3.5:1 (e.g., from 1:1 to 20:1, from 2:1 to 20:1, from 2.5:1 to 20:1, from 3:1 to 20:1, from 3:1 to 10:1, or from 4:1 to 20:1). The PPG fatty acid diester can be, for example, the dodecanoate diester, the decanoate diester, or the octanoate diester of a polypropylene glycol having from 1 to 20 PEG units (e.g., from 1 to 12 PPG units, from 2 to 10 PPG units, from 4 to 10 PPG units, or from 6 to 9 PPG units). The PPG fatty acid diester can be formed, for example, from a polypropylene glycol mixture having an average chain length of from 8 to 9 PPG units in length. In still other embodiments the reconstitutable pharmaceutical composition includes a substantially pure PPG fatty acid monoester. In other embodiments the ratio by weight of the PPG fatty acid monoester to the drug is greater than 1:1, 2:1, 2.5:1, 3.0:1, or 3.5:1 (e.g., from 1:1 to 20:1, from 2:1 to 20:1, from 2.5:1 to 20:1, from 3:1 to 20:1, from 3:1 to 10:1, or from 4:1 to 20:1). The PPG fatty acid monoester can, for example, be the dodecanoate monoester, the decanoate monoester, or the octanoate monoester of a polypropylene glycol having from 1 to 20 PPG units (e.g., from 1 to 12 PPG units, from 2 to 10 PPG units, from 4 to 10 PPG units, or from 6 to 9 PPG units). The PPG fatty acid monoester can be formed, for example, from a polypropylene glycol mixture having an average chain length of from 8 to 9 PPG units in length. In particular embodiments, the reconstitutable pharmaceutical composition is a liquid concentrate that can form an emulsion when mixed with water, or is a solid (e.g., a powder) that can be mixed with water, such as a self emulsifying composition. The reconstitutable pharmaceutical composition can be a liquid for reconstitution, a powder for reconstitution, or a suspension for reconstitution. In other embodiments, the reconstitutable pharmaceutical composition is a liquid, semi-solid, solid, or solid matrix that can be mixed with water (e.g., such as a self emulsifying composition). The reconstitutable pharmaceutical can be formulated, for example, in unit dosage form for oral administration as a hard gel capsule, soft gel capsule, effervescent tablet, or as a sprinkle.

The invention features a pharmaceutical composition in oral dosage form including: (a) cefepime, or a pharmaceutically acceptable salt thereof; and (b) an additive including a PEG fatty acid ester or PPG fatty acid ester, wherein the additive is present in an amount sufficient to increase the oral bioavailability of the drug and wherein the ratio by weight of the additive to the cefepime is greater than 1:1, 2:1, 2.5:1, 3.0:1, or 3.5:1 (e.g., from 1:1 to 20:1, from 2:1 to 20:1, from 2.5:1 to 20:1, from 3:1 to 20:1, from 3:1 to 10:1, or from 4:1 to 20:1). In particular embodiments the pharmaceutical composition includes from 10% to 80% (w/w) (e.g., from 10% to 35%, 15% to 45%, 25% to 50%, 35% to 65%, 40% to 75%, 55% to 80%, or from 60% to 80% (w/w)) of the additive (e.g., substantially pure PEG fatty acid diester, substantially pure PEG fatty acid monoester, substantially pure PPG fatty acid diester, substantially pure PPG fatty acid monoester, substantially pure PPG fatty acid diester, and/or saccharide). In particular embodiments, the pharmaceutical composition is in a unit dosage form including from 250 milligrams to 5.0 grams of cefepime, or a pharmaceutically acceptable salt thereof (e.g., from 250 mg to 500 mg, 400 mg to 750 mg, 600 mg to 1.5 g, 1.0 g to 2.5 g, 1.5 g to 3.0 g, or 2.5 g to 5.0 g). The unit dosage form can be a reconstitutable dosage form (e.g., an effervescent tablet or a sprinkle), a hard gel capsule, or a soft gel capsule. The pharmaceutical composition can include a PEG fatty acid ester can be formed, for example, from a polyethylene glycol mixture having an average chain length of from 8 to 9 PEG units in length. The pharmaceutical composition can be (i) substantially free of monoglycerides; (ii) substantially free of diglycerides; (iii) substantially free of triglycerides; (iv) substantially free of free polyethylene glycol; (v) substantially free of free polypropylene glycol; (vi) substantially free of fatty acid; and/or (vii) substantially free of glycerol. The pharmaceutical composition can include (a) a substantially pure PEG fatty acid ester; (b) a substantially pure PEG fatty acid monoester (e.g., the dodecanoate monoester, the decanoate monoester, or the octanoate monoester of a polyethylene glycol having from 1 to 20 PEG units (e.g., from 1 to 12 PEG units, from 2 to 10 PEG units, from 4 to 10 PEG units, or from 6 to 9 PEG units)); (c) a substantially pure PEG fatty acid diester (e.g., the dodecanoate diester, the decanoate diester, or the octanoate diester of a polyethylene glycol having from 1 to 20 PEG units (e.g., from 2 to 12 PEG units, from 4 to 10 PEG units, or from 6 to 9 PEG units)); (d) a substantially monodisperse PEG fatty acid ester; (e) a substantially pure PPG fatty acid ester; (f) a substantially pure PPG fatty acid monoester (e.g., the dodecanoate monoester, the decanoate monoester, or the octanoate monoester of a polypropylene glycol having from 1 to 20 PPG units (e.g., from 1 to 12 PPG units, from 2 to 10 PPG units, from 4 to 10 PPG units, or from 6 to 9 PPG units)); (g) a substantially pure PPG fatty acid diester (e.g., the dodecanoate diester, the decanoate diester, or the octanoate diester of a polypropylene glycol having from 1 to 20 PEG units (e.g., from 1 to 12 PPG units, 2 to 10 PPG units, from 4 to 10 PPG units, or from 6 to 9 PPG units)); or (h) a substantially monodisperse PPG fatty acid ester.

The invention features a pharmaceutical composition in oral dosage form including: (a) from 1.0 grams to 5.0 grams of a drug (e.g., from 1.0 g to 1.5 g, 1.0 g to 2.5 g, 1.5 g to 3.0 g, or 2.5 g to 5.0 g); and (b) an additive including a PEG fatty acid ester or PPG fatty acid ester, wherein the additive is present in an amount sufficient to increase the oral bioavailability of the drug and wherein the ratio by weight of the additive to the cefepime is greater than 1:1, 2:1, 2.5:1, 3.0:1, or 3.5:1 (e.g., from 1:1 to 20:1, from 2:1 to 20:1, from 2.5:1 to 20:1, from 3:1 to 20:1, from 3:1 to 10:1, or from 4:1 to 20:1).

In the pharmaceutical compositions of the invention, the additive can further include from 0.5% to 20% (w/w) (e.g., 0.5% to 2.5%, 1.0% to 5.0%, 2.5% to 5.0%, 5.0% to 7.5%, 7.5% to 12.5%, 12.5% to 17.5%, 17.5% to 20.0%, or from 0.75% to 12.5% (w/w)) saccharide (e.g., sucrose or fructose). In the pharmaceutical compositions of the invention, the additive can further include from 1% to 20% (w/w) (e.g., from 1% to 10%, 4% to 12%, 7.5% to 15%, or from 10% to 20% (w/w)) a polysorbate surfactant (e.g., polyoxyethylene 20 sorbitan monooleate or any other polysorbate surfactant described herein). Optionally, the pharmaceutical compositions of the invention further include an additive selected from acyl carnitines.

The formulations of the invention can be used in conjunction with any drug, such as a β-lactam antibiotic (e.g., cephalosporins, carbapenems, monobactams, penicillins, penems, carbacephems, and oxacephems). In particular embodiments, the drug is a cephalosporin, or a salt thereof (e.g., cefepime, cefalonium, cephaloridine, cefpimizole, ceftazidime, cefluprenam, cefozopran, cefpirome, cefquinome, cefmepidium, ceftaroline, ceftaroline fosamil, and salts thereof). The drug can be, for example, cefepime, or a salt thereof. In still other embodiments, the drug is a carbapenem, or a salt thereof (e.g., meropenem or ertapenem, or a salt thereof).

In a related aspect, the invention features a kit including: (a) a first container including a drug; (b) a second container including an additive including a PEG fatty acid ester or PPG fatty acid ester; and (c) instructions for mixing the contents of the first container with the contents of the second container, wherein the first container and the second container are (i) substantially free of monoglycerides; (ii) substantially free of diglycerides; (iii) substantially free of triglycerides; (iv) substantially free of free polyethylene glycol; (v) substantially free of free polypropylene glycol; (vi) substantially free of fatty acid; (vii) substantially free of glycerol; (viii) includes a substantially pure PEG fatty acid ester; (ix) includes a substantially pure PEG fatty acid monoester; (x) includes a substantially pure PEG fatty acid diester; (xi) includes a substantially monodisperse PEG fatty acid ester; (xii) includes a substantially pure PPG fatty acid ester; (xiii) includes a substantially pure PPG fatty acid monoester; (xiv) includes a substantially pure PPG fatty acid diester; or (xv) includes a substantially monodisperse PPG fatty acid ester. In particular embodiments the second container includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PEG fatty acid diester. The PEG fatty acid diester can be, for example, the dodecanoate diester, the decanoate diester, or the octanoate diester of a polyethylene glycol having from 1 to 20 PEG units (e.g., from 2 to 12 PEG units, from 4 to 10 PEG units, or from 6 to 9 PEG units). The PEG fatty acid diester can be formed, for example, from a polyethylene glycol mixture having an average chain length of from 8 to 9 PEG units in length. In other embodiments the second container includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PEG fatty acid monoester. The PEG fatty acid monoester can be, for example, the dodecanoate monoester, the decanoate monoester, or the octanoate monoester of a polyethylene glycol having from 1 to 20 PEG units (e.g., from 1 to 12 PEG units, from 2 to 10 PEG units, from 4 to 10 PEG units, or from 6 to 9 PEG units). The PEG fatty acid monoester can be formed, for example, from a polyethylene glycol mixture having an average chain length of from 8 to 9 PEG units in length. In still other embodiments the second container includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PPG fatty acid diester. The PPG fatty acid diester can be, for example, the dodecanoate diester, the decanoate diester, or the octanoate diester of a polypropylene glycol having from 1 to 20 PEG units (e.g., from 1 to 12 PPG units, 2 to 10 PPG units, from 4 to 10 PPG units, or from 6 to 9 PPG units). The PPG fatty acid diester can be formed, for example, from a polypropylene glycol mixture having an average chain length of from 8 to 9 PPG units in length. In still other embodiments the second container includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PPG fatty acid monoester. The PPG fatty acid monoester can be, for example, the dodecanoate monoester, the decanoate monoester, or the octanoate monoester of a polypropylene glycol having from 1 to 20 PPG units (e.g., from 1 to 12 PPG units, from 2 to 10 PPG units, from 4 to 10 PPG units, or from 6 to 9 PPG units). The PPG fatty acid monoester can be formed, for example, from a polypropylene glycol mixture having an average chain length of from 8 to 9 PPG units in length. In one particular embodiment of the kits of the invention, mixing the contents of the first container with the second container forms a composition including from 0.5% to 20% (w/w) (e.g., from 0.5% to 2%, 1.5% to 10%, 2.5% to 12%, or from 7.5% to 20% (w/w)) of a drug; and from 40% to 80% (w/w) (e.g., from 40% to 75%, 55% to 80%, or from 60% to 80% (w/w)) an additive including a PEG fatty acid ester or PPG fatty acid ester. The kits of the invention optionally include further instructions for mixing the contents of the first container and the contents of the second container with water to form an emulsion. The kits of the invention can be used in conjunction with any drug, such as a β-lactam antibiotic (e.g., cephalosporins, carbapenems, monobactams, penicillins, penems, carbacephems, and oxacephems). In particular embodiments, the drug is a cephalosporin, or a salt thereof (e.g., cefepime, cefalonium, cephaloridine, cefpimizole, ceftazidime, cefluprenam, cefozopran, cefpirome, cefquinome, cefmepidium, ceftaroline, ceftaroline fosamil, and salts thereof). The drug can be, for example, cefepime, or a salt thereof. In still other embodiments, the drug is a carbapenem, or a salt thereof (e.g., meropenem or ertapenem, or a salt thereof). In certain embodiments, the first container of the kit includes from 250 milligrams to 5.0 grams (e.g., from 250 mg to 500 mg, 400 mg to 750 mg, 600 mg to 1.5 g, 1.0 g to 2.5 g, 1.5 g to 3.0 g, or 2.5 g to 5.0 g) of cefepime, or a pharmaceutically acceptable salt thereof. The second container in the kit can include from 0.5 grams to 20 grams (e.g., from 500 mg to 1.5 g, 1.0 g to 1.750 g, 1.5 g to 3.5 g, 2.0 g to 6.5 g, 2.5 g to 5.5 g, or 4.5 g to 20 g) PEG fatty acid ester or PPG fatty acid ester. The PEG fatty acid ester or PPG fatty acid ester can be any substantially pure PEG fatty acid diester described herein, such as a decanoate diester of a polyethylene glycol having from 1 to 20 PEG units.

The invention further features a composition including an additive including a PEG fatty acid ester or PPG fatty acid ester, wherein the composition is (i) substantially free of monoglycerides; (ii) substantially free of diglycerides; (iii) substantially free of triglycerides; (iv) substantially free of free polyethylene glycol; (v) substantially free of free polypropylene glycol; (vi) substantially free of fatty acid; (vii) substantially free of glycerol; (viii) includes a substantially pure PEG fatty acid ester; (ix) includes a substantially pure PEG fatty acid monoester; (x) includes a substantially pure PEG fatty acid diester; (xi) includes a substantially monodisperse PEG fatty acid ester; (xii) includes a substantially pure PPG fatty acid ester; (xiii) includes a substantially pure PPG fatty acid monoester; (xiv) includes a substantially pure PPG fatty acid diester; or (xv) includes a substantially monodisperse PPG fatty acid ester. In particular embodiments the composition includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PEG fatty acid diester. The PEG fatty acid diester can be, for example, the dodecanoate diester, the decanoate diester, or the octanoate diester of a polyethylene glycol having from 1 to 20 PEG units (e.g., from 2 to 12 PEG units, from 4 to 10 PEG units, or from 6 to 9 PEG units). The PEG fatty acid diester can be formed, for example, from a polyethylene glycol mixture having an average chain length of from 8 to 9 PEG units in length. In other embodiments the composition includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PEG fatty acid monoester. The PEG fatty acid monoester can be, for example, the dodecanoate monoester, the decanoate monoester, or the octanoate monoester of a polyethylene glycol having from 1 to 20 PEG units (e.g., from 1 to 12 PEG units, from 2 to 10 PEG units, from 4 to 10 PEG units, or from 6 to 9 PEG units). The PEG fatty acid monoester can be formed, for example, from a polyethylene glycol mixture having an average chain length of from 8 to 9 PEG units in length. In still other embodiments the composition includes from 10% to 80% (w/w) (e.g., from 10% to 35%, 15% to 45%, 25% to 50%, 35% to 65%, 40% to 75%, 55% to 80%, or from 60% to 80% (w/w)) of a substantially pure PPG fatty acid diester. The PPG fatty acid diester can be, for example, the dodecanoate diester, the decanoate diester, or the octanoate diester of a polypropylene glycol having from 1 to 20 PEG units (e.g., from 1 to 12 PPG units, 2 to 10 PPG units, from 4 to 10 PPG units, or from 6 to 9 PPG units). The PPG fatty acid diester can be formed, for example, from a polypropylene glycol mixture having an average chain length of from 8 to 9 PPG units in length. The composition can further include from 2% to 20% (w/w) (e.g., from 2% to 10%, 4% to 12%, 7.5% to 15%, or from 10% to 20% (w/w)) a polysorbate surfactant (e.g., polyoxyethylene 20 sorbitan monooleate, or any other polysorbate surfactant described herein). The composition can further include from 5% to 40% (w/w) (e.g., from 5% to 10%, 8% to 25%, 15% to 35%, or from 17% to 40% (w/w)) saccharide (e.g., sucrose or fructose). The invention also features a kit including (i) the composition described above; and (ii) instructions for mixing the composition with a drug (e.g., cefepime, or a salt thereof, or any other drug described herein).

The invention also features a method of treating a bacterial infection in a subject, the method including administering to the subject any of the pharmaceutical compositions of the invention including an antibiotic, where the composition is administered in an amount effective to treat the infection.

In some embodiments, the bacterial infection is pneumonia, upper and lower respiratory tract infection, uncomplicated skin and skin structure infection, complicated skin and skin structure infection, soft tissue infection, bone and joint infection, diabetic foot infections, hospital-acquired lung infection, acute bacterial otitis media, bacterial pneumonia, complicated infection, noncomplicated infection, pyelonephritis, uncomplicated intra-abdominal infection, complicated intra-abdominal infection, deep-seated abscess, bacterial sepsis, central nervous system infection, bacteremia, wound infection, peritonitis, meningitis, infections after burn, uncomplicated and complicated urinary tract infection, gastro-intestinal tract infection, pelvic inflammatory disease, endocarditis, febrile neutropenia, and intravascular infection. In preferred embodiments, the drug is cefepime and the infection is pneumonia, febrile neutropenia, uncomplicated or complicated urinary tract infection, uncomplicated skin and skin structure infection, or complicated intra-abdominal infection.

In other embodiments, the drug is cefepime and the bacterial infection is caused by *Streptococcus pneumoniae, Pseudomonas aeruginosa, Klebsiella pneumoniae, Enterobacter* spp., *Escherichia coli, Proteus mirabilis, Staphylococcus aureus, Streptococcus pyogenes, Bacteroides fragilis*, or viridans group streptococci.

In an embodiment of any of the therapeutic methods of the invention, the subject receives intravenous antibiotics (e.g., an intravenous monobactam, penicillin, cephalosporin, penem, or carbapenem treatment) prior to the oral administration of the pharmaceutical composition of the invention. Thus, the methods and compositions of the invention can be used to compliment intravenous antibiotic dosing regimens, allowing the subject to transition to an oral dosing regimen as an out-patient treatment.

The formulations of the invention can be used in conjunction with an echinocandin class compound (e.g., caspofungin, echinocandin B, anidulafungin, pneumocandin $B_0$, aculeacin $A_\gamma$ micafungin, compound 1, compound 2, and salts thereof).

The invention features a method of treating a fungal infection in a subject by orally administering to the subject a pharmaceutical composition of the invention including an antifungal agent, wherein the composition is administered in an amount effective to treat the infection.

In some embodiments, the fungal infection is selected from tinea capitis, tinea corporis, tinea pedis, onychomycosis, perionychomycosis, pityriasis versicolor, oral thrush, vaginal candidosis, respiratory tract candidosis, biliary candidosis, esophageal candidosis, urinary tract candidosis, systemic candidosis, mucocutaneous candidosis, aspergillosis, fungal sinusitis, mucormycosis, paracoccidioidomycosis, North American blastomycosis, histoplasmosis, coccidioidomycosis, and sporotrichosis.

In particular embodiments, the fungal infection is caused by *Candida albicans, C. parapsilosis, C. glabrata, C. guillermondii, C. krusei, C. tropicalis, C. kefyr, C. lusitaniae, C. dubliniensis, Aspergillus fumigatus, A. flavus, A. terreus, A. nidulans*, or *A. niger*.

The invention also features kits, including: a) any composition of the invention; and b) instructions for administering the composition to a subject diagnosed with a bacterial infection or fungal infection.

By "acyl carnitine" is meant a chemical moiety with the formula:

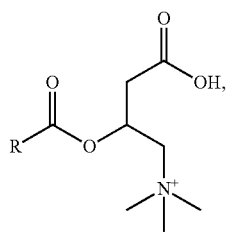

and salts thereof, wherein R is a partially-saturated straight chain or branched hydrocarbon group having between 8 and 26 carbon atoms. Acyl carnitines are derived carnitine (D or L form, or a mixture thereof) and a fatty acid. The acyl carnitine can be an ester of a fatty acid having 12 carbon atoms and 0, 1 or 2 double bonds, having 16 carbon atoms and 0, 1 or 2 double bonds, those with 18 carbon atoms and 1, 2 or 3 double bonds, those with 20 carbon atoms and 1, 2 or 4 double bonds, or those with 22 carbon atoms and 4, 5 or 6 double bonds. Acyl carnitines include, without limitation, 4, 7, 10, 13, 16, 19 docosahexanoyl carnitine, lauroyl carnitine, oleoyl carnitine, palmitoyl carnitine, decanoyl carnitine, dodecanoyl carnitine, myristoyl carnitine, and stearoyl carnitine.

As used herein, the term "administration" or "administering" refers to peroral administration of a drug to a subject.

By "an amount sufficient" is meant the amount of an additive required to increase the oral bioavailability of a drug.

As used herein, "charged low molecular weight drug" refers to a drug or salt thereof having a molecular weight of from 150 to 200, 200 to 1,200, 200 to 1,000, 200 to 800, 200 to 750, 200 to 700, 300 to 1,000, or 400 to 1,000 daltons, and bearing a charged group. Charged low molecular weight drugs include, without limitation, cephalosporins bearing a positive charge on a quaternary nitrogen atom, such as cefepime, cefalonium, cephaloridine, cefpimizole, ceftazidime, cefluprenam, cefozopran, cefpirome, cefquinome, cefmepidium, ceftaroline, and ceftaroline fosamil.

By "effective" amount is meant the amount of drug required to treat or prevent an infection or a disease associated with an infection. The effective amount of drug used to practice the invention for therapeutic or prophylactic treatment of conditions caused by or contributed to by a microbial infection varies depending upon the manner of administration, the age, body weight, and general health of the subject. Ultimately, the attending physician will decide the appropriate amount and dosage regimen. Such amount is referred to as an "effective" amount.

By "excipient" is meant those a component of a pharmaceutical composition containing a drug (e.g., a cephalosporin or carbapenem) in oral dosage form which does not increase the oral bioavailability of the drug when orally administered simultaneously with the drug. Excipients which can be used in the formulations of the invention include, without limitation, certain diluents, binders, fillers, and flavorings, the absence of which does not result in reduced oral bioavailability for a given pharmaceutical composition.

By "fatty acid" is meant an aliphatic carboxylic acid. Fatty acids include, but are not limited to, fatty acids having between 8 and 12 carbon atoms, linear and branched fatty acids, saturated and unsaturated fatty acids, and fatty acids having a hydroxyl group at the termination position of its side chain (i.e., fatty acids bearing a primary hydroxyl group). Exemplary fatty acids are caprylic acid (octanoic acid), pelargonic acid (nonanoic acid), capric acid (decanoic acid), and lauric acid (dodecanoic acid), and their primary hydroxyl forms 8-hydroxy octanoic acid, 9-hydroxy nonanoic acid, 10-hydroxy decanoic acid, and 12-hydroxy dodecanoic acid.

By "hard capsule" is meant a capsule that includes a membrane that forms a two-part, capsule-shaped, container capable of carrying a solid, semi-solid, or liquid payload of drug, additive(s), and, optionally, excipients.

As used herein, by an "increase the oral bioavailability" is meant at least 25%, 50%, 75%, 100%, or 300% greater bioavailability of an orally administered drug, as a measured average of AUC in canine subjects (e.g., as described in the examples) for an oral dosage form of the invention including a cephalosporin or carbapenem formulated with one or more additives in comparison to the same drug formulated without any additives. For these studies, the subjects have gastrointestinal tracts that have not been surgically manipulated in a manner that would alter the oral bioavailability of a drug.

By "microemulsion" is meant a clear, stable, isotropic liquid mixture of oil, water, and surfactant, optionally in combination with a cosurfactant. The aqueous phase may contain salt(s) and/or other ingredients in addition to a biologically active agent. In contrast to ordinary emulsions, microemulsions form upon simple mixing of the components and do not require the high shear conditions generally used in the formation of ordinary emulsions. The two basic types of microemulsions are direct (oil dispersed in water, o/w) and reversed (water dispersed in oil, w/o).

As used herein, the term "self-emulsifying" refers to a formulation that, upon contact with an aqueous medium, spontaneously forms an emulsion. The self-emulsifying compositions and formulations of the invention can form stable emulsions in solutions that are greater than 40%, 50%, 60%, 70%, 75%, 80%, 85%, or 90% (w/w) water. By "emulsion" is meant a suspension having a continuous aqueous phase and a dispersed lipid phase including one or more additives (e.g., a PEG fatty acid ester or PPG fatty acid ester) and a drug. Emulsions may be partially, temporarily and/or completely stable. By "stable emulsion" is meant an emulsion that will not separate into its components under the conditions for which it was made.

By "liquid dosage form" is meant a solution or suspension or emulsion from which a dose is measured out (i.e., a teaspoon, tablespoon, or a number of cubic centimeters or fluid ounces for oral administration to a subject.

As used herein, "oral bioavailability" refers to the fraction of drug absorbed following oral administration to a subject as measured by the blood circulating concentration in comparison to the blood circulating concentration observed for the 100% bioavailability observed with intravenously or intraarterially administered drug.

As used herein, the term "salt" refers to any pharmaceutically acceptable salt, such as a non-toxic acid addition salt, metal salt, or metal complex, commonly used in the pharmaceutical industry. Acid addition salts include organic acids, such as acetic, lactic, pamoic, maleic, citric, malic, ascorbic, succinic, benzoic, palmitic, suberic, salicylic, tartaric, methanesulfonic, toluenesulfonic, or trifluoroacetic acids, and inorganic acids, such as hydrochloric acid, hydrobromic acid, sulfuric acid, and phosphoric acid. Representative alkali or alkaline earth metal salts include sodium, lithium, potassium, calcium, and magnesium, among others.

As used herein, the term "PEG fatty acid ester" refers to PEG fatty acid monoesters and PEG fatty acid diesters, and mixtures thereof.

As used herein, the term "PEG fatty acid monoester" refers to $C_8$-$C_{12}$ fatty acid monoesters of polyethylene glycol.

As used herein, the term "PEG fatty acid diester" refers to $C_8$-$C_{12}$ fatty acid diesters of polyethylene glycol.

As used herein, the term "PPG fatty acid ester" refers to PPG fatty acid monoesters and PPG fatty acid diesters, and mixtures thereof.

As used herein, the term "PPG fatty acid monoester" refers to $C_8$-$C_{12}$ fatty acid monoesters of polypropylene glycol.

As used herein, the term "PPG fatty acid diester" refers to $C_8$-$C_{12}$ fatty acid diesters of polypropylene glycol.

As used herein, the term "substantially free of monoglycerides" refers to formulations of the invention including less than 1%, 0.5%, 0.25%, or 0.05% (w/w) monoglycerides (i.e., fatty acid monoesters of glycerol).

As used herein, the term "substantially free of diglycerides" refers to formulations of the invention including less than 5%, 3%, 1%, 0.5%, 0.1%, or 0.05% (w/w) diglycerides (i.e., fatty acid diesters of glycerol).

As used herein, the term "substantially free of triglycerides" refers to formulations of the invention including less than 1%, 0.5%, 0.25%, or 0.05% (w/w) triglycerides (i.e., fatty acid triesters of glycerol).

As used herein, the term "substantially free of free polyethylene glycol" refers to formulations of the invention including less than 15%, 5%, 3%, 1%, 0.5%, 0.1%, or 0.05% (w/w) chemically unmodified polyethylene glycol.

As used herein, the term "substantially free of free polypropylene glycol" refers to formulations of the invention including less than 5%, 3%, 1%, 0.5%, 0.1%, or 0.05% (w/w) chemically unmodified polypropylene glycol.

As used herein, the term "substantially free of fatty acid" refers to formulations of the invention including less than 10%, 8%, 6%, 4%, 2%, 1%, 0.5%, 0.25%, or 0.05% (w/w) fatty acids and fatty acid salts.

As used herein, the term "substantially free of glycerol" refers to formulations of the invention including less than 2%, 1%, 0.5%, 0.25%, or 0.05% (w/w) glycerol.

As used herein, the term "substantially monodisperse" refers to PEG fatty acid esters and PPG fatty acid esters in which the size distribution of the polyether component (i.e., the polyethylene glycol or polypropylene glycol component) is either completely monodisperse, or a mixture in which 90%, 94%, 96%, 98%, or 99% (w/w) of the polyethers are identical in length (e.g., from 1 to 20 repeating units in length). A PEG fatty acid ester or PPG fatty acid ester formed from a polyether that is not substantially monodisperse is referred to herein as "polydisperse." The PEG fatty acid esters and PPG fatty acid esters used in the formulations of the invention can include either monodisperse (i.e., substantially a single molecular weight) or polydisperse polyether moieties of a predetermined size or size range (e.g., PEG1 to PEG 40).

As used herein, the term "substantially pure PEG fatty acid ester" refers to formulations of the invention including one or more a PEG fatty acid esters formed from a fatty acid of chain length n and including less than 20%, 15%, 10%, 5%, 3%, 1%, 0.5%, or 0.1% (w/w) fatty acid esters formed from a fatty acid of chain length other than n. For example, a formulation including substantially pure C10 PEG fatty acid ester includes less than 20%, 15%, 10%, 5%, 3%, 1%, 0.5%, or 0.1% (w/w) PEG fatty acid esters formed from C8, C9, C11, and C12 fatty acids.

As used herein, the term "substantially pure PEG fatty acid monoester" refers to formulations of the invention including a PEG fatty acid monoester formed from a fatty acid of chain length n, and (i) including less than 20%, 15%, 10%, 5%, 3%, 1%, 0.5%, or 0.1% (w/w) PEG fatty acid diesters, and (ii) including less than 6%, 5%, 3%, 1%, 0.5%, 0.1%, or 0.05% (w/w) PEG fatty acid monoesters formed from a fatty acid of chain length other than n. For example, a formulation including substantially pure C10 PEG fatty acid monoester includes less than 6%, 5%, 3%, 1%, 0.5%, 0.1%, or 0.05% (w/w) PEG fatty acid monoesters formed from C8, C9, C11, and C12 fatty acids.

As used herein, the term "substantially pure PEG fatty acid diester" refers to formulations of the invention including a PEG fatty acid diester formed from a fatty acid of chain length n, and (i) including less than 20% 15%, 10%, 5%, 3%, 1%, 0.5%, or 0.1% (w/w) PEG fatty acid monoesters, and (ii) including less than 6%, 5%, 3%, 1%, 0.5%, 0.1%, or 0.05% (w/w) PEG fatty acid diesters formed from a fatty acid of chain length other than n. For example, a formulation including substantially pure C10 PEG fatty acid diester includes less than 6%, 5%, 3%, 1%, 0.5%, 0.1%, or 0.05% (w/w) PEG fatty acid diesters formed from C8, C9, C11, and C12 fatty acids.

As used herein, the term "substantially pure PPG fatty acid ester" refers to formulations of the invention including one or more a PPG fatty acid esters formed from a fatty acid of chain length n and including less than 20%, 15%, 10%, 5%, 3%, 1%, 0.5%, or 0.1% (w/w) fatty acid esters formed from a fatty acid of chain length other than n. For example, a formulation including substantially pure C10 PPG fatty acid ester includes less than 20%, 15%, 10%, 5%, 3%, 1%, 0.5%, or 0.1% (w/w) PPG fatty acid esters formed from C8, C9, C11, and C12 fatty acids.

As used herein, the term "substantially pure PPG fatty acid monoester" refers to formulations of the invention including a PPG fatty acid monoester formed from a fatty acid of chain length n, and (i) including less than 20%, 15%, 10%, 5%, 3%, 1%, 0.5%, or 0.1% (w/w) PPG fatty acid diesters, and (ii) including less than 6%, 5%, 3%, 1%, 0.5%, 0.1%, or 0.05% (w/w) PPG fatty acid monoesters formed from a fatty acid of chain length other than n. For example, a formulation including substantially pure C10 PPG fatty acid monoester includes less than 6%, 5%, 3%, 1%, 0.5%, 0.1%, or 0.05% (w/w) PPG fatty acid monoesters formed from C8, C9, C11, and C12 fatty acids.

As used herein, the term "substantially pure PPG fatty acid diester" refers to formulations of the invention including a PPG fatty acid diester formed from a fatty acid of chain length n, and (i) including less than 20%, 15%, 10%, 5%, 3%, 1%, 0.5%, or 0.1% (w/w) PPG fatty acid monoesters, and (ii) including less than 6%, 5%, 3%, 1%, 0.5%, 0.1%, or 0.05% (w/w) PPG fatty acid diesters formed from a fatty acid of chain length other than n. For example, a formulation including substantially pure C10 PPG fatty acid diester includes less than 6%, 5%, 3%, 1%, 0.5%, 0.1%, or 0.05% (w/w) PPG fatty acid diesters formed from C8, C9, C11, and C12 fatty acids.

By "soft capsule" is meant a capsule molded into a single container carrying a liquid payload or semi-solid containing drug, additive(s), and, optionally, excipients (i.e., including emulsified, such as from a self emulsifying formulation, and non-emulsified formulations).

By "solid dosage form" is meant a pharmaceutical composition that is a solid or semisolid under ambient conditions. A solid dosage form can be prepared, for example, from a liquid or semisolid pay load of drug, additives, and excipients absorbed into a solid matrix such as sucrose, maltose, cellulose, or Neusilin, among other solid matrices, to form a finished product that is a solid dosage form. The solid dosage form can be filled into a capsule or into a sachet for reconstitution in water.

By "subject" is meant an animal, e.g., a human.

As used herein, the term "treating" refers to administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

The term "unit dosage form" refers to physically discrete units suitable as unitary dosages, such as a tablet, caplet, hard capsule, soft capsule, or sachet, each unit containing a predetermined quantity of drug, and including any predetermined amount of a powder or liquid for reconstitution in a liquid prior to administration.

Other features and advantages of the invention will be apparent from the following detailed description and the claims.

DETAILED DESCRIPTION

The invention provides stable pharmaceutical formulations including a drug (e.g., a β-lactam antibiotic or echinocandin class compound) formulated with a PEG fatty acid monoester, PEG fatty acid diester, PPG fatty acid monoester, or PEG fatty acid diester, optionally in combination with a saccharide (e.g., sucrose). The formulations are useful for increasing the oral bioavailability of the drug. β-lactam antibiotics that can be formulated as described herein include cephalosporins, carbapenems (e.g., meropenem (Merrem®)), monobactams (aztreonam [Azactam®]), penicillins, penems (faropenem), carbacephems (loracarbef [Lorabid®]), and oxacephems (flomoxef and latamoxef [Moxalactam®]).

Cephalosporins

The formulations of the invention can be used to increase the oral bioavailability of cephalosporins. Cephalosporins are a class of β-lactam antibiotics with broad-spectrum activity against Gram-positive and Gram-negative bacteria. Cephalosporins share a core structure shown by formula (I), where $R_1$ and $R_2$ can be any substituent.

Cephalosporins which can be used in the unit dosage forms of the invention include, for example, cefepime (Maxipime®, Maxcef®, Cepimax®, Cepimex®, and Axepim®; 1-[[6R, 7R)-7-[2-(2-amino-4-thiazolyl)glyoxylamido]-2-carboxy-8-oxo-5-thia-1-azabicyclo[4.2.0]oct-2-en-3-yl]methyl]-1-methlypyrrolidinium chloride, 72-(Z)—(O-methyloxime), monohydrochloride, monohydrate), cefotaxime (Claforan®, Taxime®; (6R,7R,Z)-3-(acetoxymethyl)-7-(2-(2-aminothiazol-4-yl)-2-(methoxyimino)acetamido)-8-oxo-5-thia-1-azabicyclo[4.2.0]oct-2-ene-2-carboxylic acid), ceftriaxone (Rocephin®), cefacetrile (cephacetrile), cefadroxil (cefadroxyl; duricef), cefoselis, cephalexin (cephalexin; Keflex®), cefaloglycin (cephaloglycin), cefalonium (cephalonium), cephaloridine (cefaloridine), cefalotin (cephalothin; Keflin®), cefapirin (cephapirin; Cefadryl®), cefatrizine, cefazaflur, cefazedone, cefazolin (cephazolin; Ancef®, Kefzol®), cefradine (cephradine; Velosef®), cefroxadine, ceftezole, cefaclor (Ceclor®, Distaclor®, Keflor®, Raniclor®), cefonicid (Monocid®), cefprozil (cefproxil; Cefzil®), cefuroxime (Zinnat®, Zinacef®, Ceftin®, Biofuroksym®), cefuroxime axetil (Ceftin®), cefuzonam, cefbuperazone, cefmetazole (Zefazone®), cefminox, cefotetan (Apatef®, Cefotan®), cefoxitin (Mefoxin®), cefcapene, cefdaloxime, cefdinir (Omnicef®, Kefnir®), cefditoren, cefetamet, cefixime (Suprax®), cefmenoxime, cefodizime, cefpimizole, cefpodoxime (Vantin®, Pecef®), cefteram, ceftibuten (Cedax®), ceftiofur, ceftiolene, ceftizoxime (Cefizox®), cefoperazone (Cefobid®), ceftazidime (Fortum®, Fortaz®), cefclidine, cefluprenam, cefoselis, cefozopran, cefpirome (Cefrom®), cefquinome, ceftobiprole (Medocaril®), cefaclomezine, cefaloram, cefaparole, cefcanel, cefedrolor, cefempidone, cefetrizole, cefivitril, cefmatilen, cefmepidium, cefovecin, cefoxazole, cefrotil, cefsumide, ceftaroline, ceftaroline fosamil (Teflaro™), ceftioxide, cefuracetime, ceftobiprole, or other derivatives or analogs of 7-aminocephalosporanic acid. The structures of cefepime, cefotaxime, and ceftriaxone are shown below.

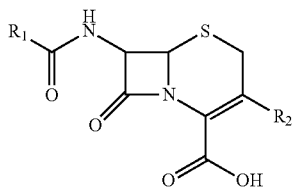

cefepine cefotaxime (I)

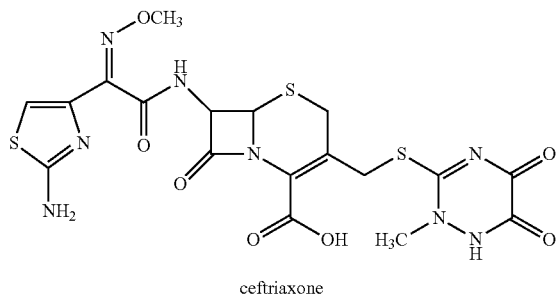

ceftriaxone

The formulations of the invention can be used to enhance the oral bioavailability of cephalosporins having a permanent positive charge on a quaternary nitrogen atom (e.g., cefepime, cefalonium, cephaloridine, cefpimizole, ceftazidime, cefluprenam, cefozopran, cefpirome, cefquinome, cefmepidium, ceftaroline, or ceftaroline fosamil).

Carbapenems

The formulations of the invention can be used to increase the oral bioavailability of carbapenems. Carbapenems are a class of beta-lactam antibiotics with broad spectrum antibacterial activity. The carbapenems are structurally very similar to the penicillins, but the sulfur atom in the structure has been replaced with a carbon atom, as shown in formula (II) below:

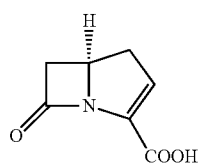

(II)

This structural modification renders them highly resistant to beta-lactamases. Carbapenem antibiotics were originally developed from thienamycin, a naturally-derived product of *Streptomyces* cattleya. Carbapenems include imipenem, meropenem, ertapenem, doripenem, panipenem/betamipron, biapenem, and PZ-601. Structures of meropenem and ertapenem are given below:

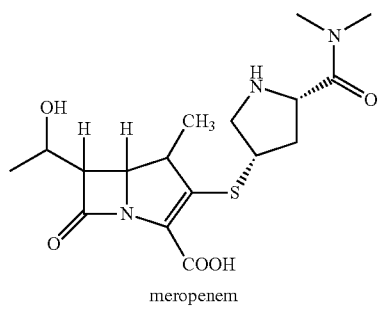

meropenem

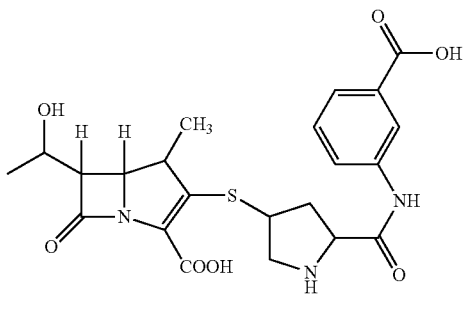

ertapenem

Echinocandin Class Compounds

The formulations of the invention can be used to increase the oral bioavailability of echinocandin class compounds. Echinocandin class compounds are inhibitors of the synthesis of 1,3-β-D-glucan and include an antibiotic cyclic lipohexapeptide having the backbone depicted in formula (III).

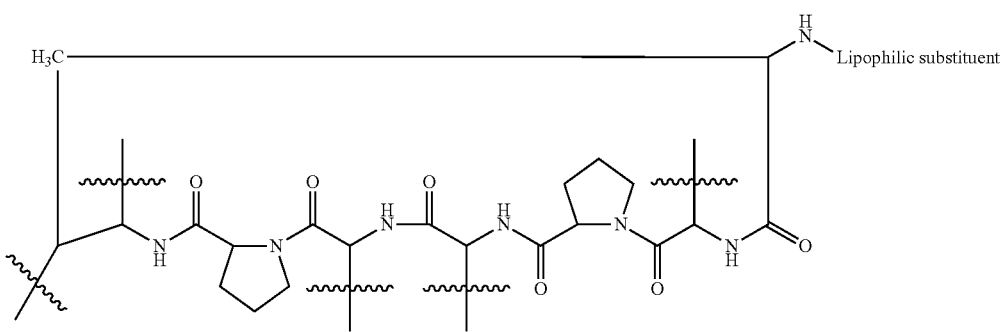

backbone for an echinocandin class compounds

Echinocandin class compounds include, without limitation, caspofungin, echinocandin B, anidulafungin, pneumocandin $B_0$, aculeacin $A_\gamma$, micafungin, and their derivatives. The echinocandin class compound can be selected from those described in PCT Publication No. WO 2011/025875, and U.S. provisional Ser. No. 61/448,807, filed Mar. 3, 2011, each of are incorporated herein by reference.

Echinocandin class compounds can be synthesized, for example, by coupling functionalized or unfunctionalized echinocandin class compounds with the appropriate acyl, alkyl and/or amino groups under standard reaction conditions (see PCT Publication No. WO 2011/025875, and U.S. provisional Ser. No. 61/448,807). Typically, the semi-synthetic echinocandin class compounds are made by modifying the naturally occurring echinocandin scaffold. For example, pneumocandin $B_0$ is prepared by fermentation reactions; where fermentation and mixed broths produce a mixture of products which are then separated to produce pneumocandin $B_0$, which is used in the synthesis of caspofungin (see U.S. Pat. No. 6,610,822, which describes extractions of the echinocandin class compounds, such as, pneumocandin $B_0$, WF 11899 and echinocandin B by performing several extraction processes; and see U.S. Pat. No. 6,610,822, which describes methods for purifying the crude extracts). For semi-synthetic approaches to echinocandin class compounds of the invention, the stereochemistry of the compound will be dictated by the starting material. Thus, the stereochemistry of the unnatural echinocandin derivatives will typically have the same stereochemistry as the naturally occurring echinocandin scaffold from which they are derived. Accordingly, any of echinocandin B, anidulafungin, micafungin, and caspofungin, can be used as a starting material in the synthesis of echinocandin class compounds which share the same stereochemical configuration at each of the amino acid residues found in the naturally occurring compound.

The echinocandin class compound formulated as described herein can be a compound of formula (IV):

$O]_bCH\{CH_2[OCH_2(CH_2)_c]_dX_5\}_2$, $O[CH_2(CH_2)_a O]_bCH\{CH_2[OCH_2(CH_2)_c]_dX_5\}_2$, $NH(CH_2CH_2NH)_rCH_2CH_2X_5$, $NHCH_2(CH_2)_qX_6$, or $OCH_2(CH_2)_qX_6$; $R^T$ is n-pentyl, sec-pentyl, or iso-pentyl; $X_1$ is $NH_2$, $NHR^{A1}$, $NR^{A1}R^{A2}$, or $NR^{A1}R^{A2}R^{A3}$; $X_2$ is OH or $OR^{B1}$; $X_3$ is $NH_2$, $NHR^{C1}$, $NR^{C1}R^{C2}$, or $NR^{C1}R^{C2}R^{C3}$; $X_4$ is $NR^{D1}R^{D2}R^{D3}$; each $X_5$ is, independently, selected from OH, $OR^{E1}$, $NH_2$, $NHR^{E1}$, $NR^{E1}R^{E2}$, and $NR^{E1}R^{E2}R^{E3}$; $X_6$ is selected from $NR^{F1}R^{F2}R^{F3}$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); n is an integer from 1 to 5 (e.g., 1, 2, 3, 4, or 5); m is an integer from 1 to 5 (e.g., 1, 2, 3, 4, or 5); p is an integer from 1 to 5 (e.g., 1, 2, 3, 4, or 5); r is an integer from 1 to 5 (e.g., 1, 2, 3, 4, or 5); q is an integer from 1 to 3 (e.g., 1, 2, or 3); and each of $R^{A1}$, $R^{A2}$, $R^{A3}$, $R^{B1}$, $R^{C1}$, $R^{C2}$, $R^{C3}$, $R^{D1}$, $R^{D2}$, $R^{D3}$, $R^{E1}$, $R^{E2}$, $R^{E3}$, $R^{F1}$, $R^{F2}$, and $R^{F3}$ is, independently, selected from $CH_3$, $CH_2CH_3$, $CH_2CH_2CH_3$, and $CH(CH_3)_2$, and pharmaceutically acceptable salts thereof. For example, one of $X_1$, $X_3$, $X_4$, and $X_5$ can be selected from $N(CH_3)_3^+$ and $N(CH_2CH_3)_3^+$. The echinocandin class compound of formula (IV) can be one in which $R^1$ is $NHCH_2CH_2N(CH_3)_3^+$ and $R^T$ is n-pentyl (referred to herein as "compound 1"); or one in which $R^1$ is $OCH_2CH_2N(CH_3)_3^+$, and $R^T$ is n-pentyl (referred to herein as "compound 2").

Formulation

The invention features formulations having additives including PEG fatty acid monoester, PEG fatty acid diester, PPG fatty acid monoester, or PEG fatty acid diester, optionally in combination with a saccharide (e.g., sucrose) and/or an acyl carnitine. These additives increase the oral bioavailability of a drug.

PEG Fatty Acid Esters

PEG fatty acid esters are fatty acid mono- and di-esters of polyethylene glycol (e.g., fatty acid esters of PEG 100, PEG 200, PEG 400, PEG 600, PEG 800, PEG 1000, PEG 1200, etc.). In particular embodiments, the PEG is from 1 to 25 polyethylene glycol units in length. The fatty acid portion of the PEG fatty acid ester is typically an aliphatic carboxylic acid, such as fatty acids having between 8 and 12 carbon atoms, linear and branched fatty acids, saturated and unsaturated fatty acids, and fatty acids having a hydroxyl group at

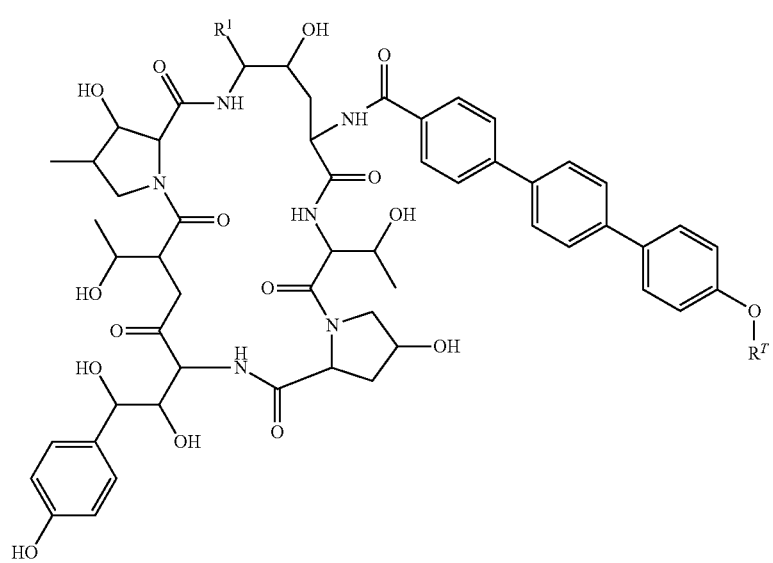

(IV)

In formula (IV), $R^1$ is $O(CH_2CH_2O)_nCH_2CH_2X_1$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_pCH_2CH_2X_3$, $NH(CH_2CH_2O)_pCH_2CH_2X_3$, $NHCH_2CH_2X_4$, $NH[CH_2(CH_2)_a$ the termination position of its side chain (i.e., fatty acids bearing a primary hydroxyl group). Exemplary fatty acids that can be used in the PEG fatty acid esters of the invention include, without limitation, caprylic acid (octanoic acid), pelargonic acid (nonanoic acid), capric acid (decanoic acid), and lauric acid (dodecanoic acid), and their primary hydroxyl forms 8-hydroxy octanoic acid, 9-hydroxy nonanoic acid, 10-hydroxy decanoic acid, and 12-hydroxy dodecanoic acid.

PEG fatty acid esters can be synthesized as described in the examples.

PPG Fatty Acid Esters

PPG fatty acid esters are fatty acid mono- and di-esters of polypropylene glycol (e.g., fatty acid esters of PPG 100, PPG 200, PPG 400, PPG 600, PPG 800, PPG 1000, PPG 1200, etc.). In particular embodiments, the PPG is from 2 to 25 polyproylene glycol units in length. The fatty acid portion of the PPG fatty acid ester is typically an aliphatic carboxylic acid, such as fatty acids having between 8 and 12 carbon atoms, linear and branched fatty acids, saturated and unsaturated fatty acids, and fatty acids having a hydroxyl group at the termination position of its side chain (i.e., fatty acids bearing a primary hydroxyl group). Exemplary fatty acids that can be used in the PPG fatty acid esters of the invention include, without limitation, caprylic acid (octanoic acid), pelargonic acid (nonanoic acid), capric acid (decanoic acid), and lauric acid (dodecanoic acid), and their primary hydroxyl forms 8-hydroxy octanoic acid, 9-hydroxy nonanoic acid, 10-hydroxy decanoic acid, and 12-hydroxy dodecanoic acid.

PPG fatty acid esters can be synthesized using methods analogous to those described in the examples for PEG fatty acid esters.

Acyl Carnitines

Acyl carnitines can be used in the oral dosage forms of the invention, in either their zwitter ion form or salt form. Acyl carnitines can be derived carnitine (D or L form, or a mixture thereof) and a fatty acid including, without limitation, fatty acids having 12 carbon atoms and 0, 1 or 2 double bonds, fatty acids having 16 carbon atoms and 0, 1 or 2 double bonds, those with 18 carbon atoms and 1, 2 or 3 double bonds, those with 20 carbon atoms and 1, 2 or 4 double bonds, and those with 22 carbon atoms and 4, 5 or 6 double bonds. Exemplary acyl carnitines which are useful additives in the formulations of the invention include lauroyl carnitine, oleoyl carnitine, palmitoyl carnitine, decanoyl carnitine, dodecanoyl carnitine, myristoyl carnitine, and stearoyl carnitine. For example, the pharmaceutical compositions of the invention can further include from 1.2% to 25% (w/w) acyl carnitine (e.g., from 1.2% to 5% 3% to 12%, 7% to 18%, 10% to 20%, or 15% to 25% (w/w) acyl carnitine), such as palmitoyl carnitine, lauroyl carnitine, or any other acyl carnitine described herein.

Polysorbate Surfactants

Polysorbate surfactants can be used in the oral dosage forms of the invention. Polysorbate surfactants are oily liquids derived from pegylated sorbitan esterified with fatty acids. Common brand names for Polysorbates include Alkest, Canarcel and Tween. Polysorbate surfactants include, without limitation, polyoxyethylene 20 sorbitan monolaurate (TWEEN 20), polyoxyethylene (4) sorbitan monolaurate (TWEEN 21), polyoxyethylene 20 sorbitan monopalmitate (TWEEN 40), polyoxyethylene 20 sorbitan monostearate (TWEEN 60); and polyoxyethylene 20 sorbitan monooleate (TWEEN 80).

Therapy

The pharmaceutical compositions described herein can be used to treat disease. For example, antibacterial compounds can be orally administered for the treatment or prevention of bacterial infections. Antifungal compounds can be orally administered for the treatment or prevention of bacterial infections.

Bacterial infections which can be treated using the unit dosage forms of the invention include pneumonia, upper and lower respiratory tract infection, uncomplicated skin and skin structure infection, complicated skin and skin structure infection, soft tissue infection, bone and joint infection, hospital-acquired lung infection, acute bacterial otitis media, bacterial pneumonia, complicated infection, noncomplicated infection, pyelonephritis, uncomplicated intra-abdominal infection, complicated intra-abdominal infection, deep-seated abscess, bacterial sepsis, central nervous system infection, bacteremia, wound infection, peritonitis, meningitis, infections after burn, uncomplicated and complicated urinary tract infection, gastro-intestinal tract infection, pelvic inflammatory disease, endocarditis, febrile neutropenia, and intravascular infection. The formulations of the invention can specifically be used to treat any infection which the drug within the formulation has been previously been reported to be an effective treatment (e.g., when administered intravenously).

Administration of Cefepime

Cefepime is indicated in the treatment of the following infections caused by susceptible strains of the designated microorganisms: pneumonia (moderate to severe) caused by *Streptococcus pneumoniae*, including cases associated with concurrent bacteremia, *Pseudomonas aeruginosa, Klebsiella pneumoniae*, or *Enterobacter* species; empiric treatment of febrile neutropenic subjects; uncomplicated and complicated urinary tract infections (including pyelonephritis) caused by *Escherichia coli* or *Klebsiella pneumoniae*, when the infection is severe, or caused by *Escherichia coli, Klebsiella pneumoniae*, or *Proteus mirabilis*, when the infection is mild to moderate, including cases associated with concurrent bacteremia with these microorganisms; uncomplicated skin and skin structure infections caused by *Staphylococcus aureus* (methicillin-susceptible strains only) or *Streptococcus pyogenes*; complicated intra-abdominal infections (used in combination with metronidazole) caused by *Escherichia coli*, viridans group streptococci, *Pseudomonas aeruginosa, Klebsiella pneumoniae, Enterobacter*, or *Bacteroides fragilis*.

Administration of Meropenem

Meropenem is indicated in the treatment of the following infections caused by susceptible strains of the designated microorganisms: complicated appendicitis and peritonitis caused by susceptible isolates of viridans group streptococci, *Escherichia coli, Klebsiella pneumoniae, Pseudomonas aeruginosa, Bacteroides fragilis, B. thetaiotaomicron*, and *Peptostreptococcus* species; complicated skin and skin structure infections caused by susceptible isolates of *Staphylococcus aureus* (beta-lactamase and non-beta-lactamase-producing, methicillin-susceptible isolates only), *Streptococcus pyogenes, S. agalactiae*, viridans group streptococci, *Enterococcus faecalis* (excluding vancomycin-resistant isolates), *P. aeruginosa, E. coli, Proteus mirabilis, B. fragilis*, and *Peptostreptococcus* species; and bacterial meningitis caused by susceptible isolates of *S. pneumoniae, Haemophilus influenzae* (beta-lactamase and non-beta-lactamase-producing isolates), and *Neisseria meningitidis*.

Administration of Echinocandin Class Compounds

Formulations of the invention including an echinocandin class compound can be used to treat fungal infections. The fungal infection being treated can be an infection selected from tinea capitis, tinea corporis, tinea pedis, onychomycosis, perionychomycosis, pityriasis versicolor, oral thrush, vaginal candidosis, respiratory tract candidosis, biliary candidosis, esophageal candidosis, urinary tract candidosis, systemic candidosis, mucocutaneous candidosis, aspergillosis, fungal sinusitis, mucormycosis, paracoccidioidomycosis, North American blastomycosis, histoplasmosis, coccidioidomycosis, or sporotrichosis. For example, the infection being treated is an infection by *Candida albicans, C. parapsilosis, C. glabrata, C. guilliermondii, C. krusei, C. tropicalis, C. kefyr, C. lusitaniae, C. dubliniensis, Aspergillus fumigatus, A. flavus, A. terreus, A. nidulans,* or *A. niger.*

The following examples are put forth so as to provide those of ordinary skill in the art with a complete disclosure and description of how the methods and compounds claimed herein are performed, made, and evaluated, and are intended to be purely exemplary of the invention and are not intended to be limiting.

EXAMPLE 1

Synthesis of Fatty Acid Esters

Fatty acid esters for use in the formulations of the invention can be synthesized as described below.

Synthesis of C10 Mono and Di-Esters of PEG400

Polyethylene glycol 400 (PEG-8; 25.0 g) was dissolved in dichloromethane and cooled to 10° C. A first equivalent of decanoyl chloride (11.83 g) was added over at least 30 minutes before being left to stir for at least 16 hours at between 10° C. and room temperature. The solution was once again cooled to 10° C. and a second equivalent of decanoyl chloride (11.83 g) was added. The mixture was left to stir for at least 16 hours at between 10° C. and room temperature before being cooled to 0° C. and quenched with water followed by an aqueous saturated sodium bicarbonate solution. The layers were separated and the organic layer was washed three times with a saturated aqueous sodium bicarbonate solution followed by a water wash. The organic layer was dried over sodium sulfate and concentrated to give the title compounds as a colorless to faint color oil. The resulting product was further dried under vacuum overnight for two days at 35° C. under constant stirring to remove traces of dichloromethane. Yield: 32 grams. HPLC/ELSD: 95% PEG400 didecanoate (PEG400 diester); 5% PEG400 decanoate (PEG400 monoester); and 0.28% capric acid.

Synthesis of C10 Mono and Di-Esters of PEG200

The above method was carried out using polyethylene glycol 200 (PEG-4, 12.4 g). Yield: 16 grams. HPLC/ELSD: 97% PEG200 didecanoate (PEG200 diester) and 3% PEG200 decanoate (PEG200 monoester).

Synthesis of C10 Mono and Di-Esters of PEG1000:

The method above was carried out using polyethylene glycol 1000 (PEG-22, 62.0 g). Yield: 62 grams. HPLC/ELSD: 93% PEG1000 didecanoate (PEG1000 diester) and 7% PEG1000 decanoate (PEG1000 monoester).

Synthesis of C8 Esters of PEG400

Polyethylene glycol 400 (PEG-8; 50.4 g) was dissolved in dichloromethane and cooled to 10° C. Octanoyl chloride (2.5 eq, 30.25 g) was added over at least 30 minutes before being left to stir for at least 16 hours at between 10° C. and room temperature. The solution was once again cooled to 10° C. and the remaining octanoyl chloride (2.5 eq, 30.25 g) was added. The mixture was left to stir for at least 16 hours at between 10° C. and room temperature before being cooled to 0° C. and quenched with water followed by an aqueous saturated sodium bicarbonate solution. The layers were separated and the organic layer was washed three times with a saturated aqueous sodium bicarbonate solution followed by a water wash. The organic layer was dried over sodium sulfate and concentrated to give the title compounds as a colorless to faint color oil. The resulting product was further dried under vacuum overnight for two days at 35° C. under constant stirring to remove traces of dichloromethane. Yield: 57 grams. HPLC/ELSD: 75% PEG400 dioctanoate (PEG400 diester); 24% PEG400 octanoate (PEG400 monoester).

EXAMPLE 2

Emulsion Formulation Using a Mixture of Fatty Acid Monoesters and Fatty Acid Diesters of PEG 400

Cefepime was formulated as an emulsion contained in a liquid filled capsule. A mixture of mono-decanoate and di-decanoate esters of PEG 400 and Tween 80 were mixed with vortexing for 30 seconds. To this mixture was added, 500 mg of cefepime hydrochloride, and the resulting mixture was vortexed for an additional 60 seconds. Prior to reconstitution, the formulation was kept at room temperature for a minimum of three hours. The formulation was reconstituted with 3.3 mL of pH 5.2 sodium acetate buffer (0.1 M) and vortexed for 30-60 seconds, until a homogenous milky white solution/emulsion was formed. The resulting emulsion was sonicated in a water bath for ~10-15 minutes at ~30° C. The emulsion was vortexed gently for 60 seconds immediately prior to filling into hard gelatin capsule (size 11). The contents of the capsule are provided in Table 1.

TABLE 1

Formulation 1.

| Ingredient | Function | mg/dose | % w/w |
|---|---|---|---|
| Mixed esters of PEG 400[a] | "permeation enhancer" | 2000 mg | 32.8% |
| Tween 80 | Surfactant/Emulsifier | 300 mg | 4.9% |
| Cefepime HCl | Active | *500 mg | 8.2% |
| Buffer, pH 5.2, Na acetate | Medium | 3.3 mL | 54.1% |

[a]Composition: free capric acid (0.2 w/w %), free PEG 400 (0.4% by HPLC), PEG 400 monodecanoate (58.8% fatty acid ester fraction by HPLC), and PEG 400 didecanoate (41.2% fatty acid ester fraction by HPLC).
b. *as free base The filled capsules were dosed shortly after filling (see Example 6).

EXAMPLE 3

Emulsion Formulation Using a Substantially Pure Fatty Acid Diester of PEG 400

Cefepime was formulated as an emulsion contained in a liquid filled capsule. Substantially pure PEG 400 didecanoate and Tween 80 were mixed by vortexing for 30 seconds. To this mixture was added, 500 mg of cefepime hydrochloride, and the resulting mixture was vortexed for an additional 60 seconds. Prior to reconstitution, the formulation was kept at room temperature for a minimum of three hours. The formulation was reconstituted with 3.3 mL of pH 5.2 Sodium acetate buffer (0.1 M) and vortexed for 30-60 seconds, until a milky white suspension/emulsion was formed. The resulting suspension/emulsion was sonicated in a water bath for ~10-15 minutes at ~30° C. The suspension/emulsion was vortexed gently for 60 seconds immediately prior to filling into hard gelatin capsule (size 11). The contents of the capsule are provided in Table 2.

TABLE 2

Formulation 2.

| Ingredient | Function | mg/dose | % w/w |
|---|---|---|---|
| PEG 400 didecanoate[a] | "permeation enhancer" | 2000 mg | 32.8% |
| Tween 80 | Surfactant/ Emulsifier | 300 mg | 4.9% |
| Cefepime HCl | Active | *500 mg | 8.2% |
| Buffer, pH 5.2, Na acetate | Medium | 3.3 mL | 54.1% |

[a]Composition: free capric acid (0 w/w %), free PEG 400 (0.1% by HPLC), PEG 400 monodecanoate (0.9% fatty acid ester fraction by HPLC), and PEG 400 didecanoate (99.1% fatty acid ester fraction by HPLC).
b. *as free base The filled capsules were dosed shortly after filling (see Example 6).

EXAMPLE 4

Emulsion Formulation Using a Substantially Pure Diester of PEG 400, Captex 1000, and Monocaprin Cefepime was formulated as an emulsion contained in a liquid filled capsule. Captex 1000 and monocaprin were dry mixed and the mixture was heated at 40-45° C. using a hot plate or water bath until completely melted. To the melted mixture was added substantially pure PEG 400 didecanoate and Tween 80 and the mixture was vortexed for 30 seconds. To this mixture was added 540 mg of cefepime hydrochloride USP, and the resulting mixture was vortexed for an additional 60 seconds. Prior to reconstitution, the formulation was kept at room temperature for a minimum of three hours. The formulation was reconstituted with 3.6 mL of pH 5.2 sodium acetate buffer (0.1 M) and mixture vortexed for 30-60 seconds, until a milky white suspension/emulsion was formed. The resulting suspension/emulsion was sonicated in a water bath for ~10-15 minutes at ~30° C. The suspension/emulsion was then vortexed gently for 60 seconds immediately prior to filling into hard gelatin capsule (size 11). The contents of the capsule are provided in Table 3.

TABLE 3

Formulation 3.

| Ingredient | Function | mg/dose | % w/w |
|---|---|---|---|
| Captex 1000 (triglyceryl decanoate) | "permeation enhancer" | 432 mg | 6.5% |
| Glyceryl mono decanoate (monoglyceryl decanoate) | permeation enhancer" "P4" | 108 mg | 1.6% |
| Tween 80 | Surfactant/ Emulsifier | 300 mg | 4.5% |
| PEG 400 didecanoate[a] | "permeation enhancer" | 1620 mg | 24.5% |
| Cefepime HCl | Active | *540 mg | 8.2% |
| Buffer, pH 5.2, Na Acetate | Medium | 3.6 mL | 54.5% |

[a]Composition: free capric acid (0 w/w %), free PEG 400 (0.1% by HPLC), PEG 400 monodecanoate (0.9% fatty acid ester fraction by HPLC), and PEG 400 didecanoate (99.1% fatty acid ester fraction by HPLC).
b. *as free base The filled capsules were dosed shortly after filling (see Example 6).

EXAMPLE 5

Emulsion Formulation Using a Substantially Pure Fatty Acid Diester of PEG 400, Captex 1000, and Monocaprin Cefepime was formulated as an emulsion contained in a liquid filled capsule. Captex 1000 and monocaprin were dry mixed and the mixture was heated at 40-45° C. using a hot plate or water bath until completely melted. To the melted mixture was added substantially pure PEG 400 didecanoate and Tween 80 and the mixture was vortexed for 30 seconds. To this mixture was added 540 mg of cefepime hydrochloride USP, and the resulting mixture was vortexed for an additional 60 seconds. Prior to reconstitution, the formulation was kept at room temperature for a minimum of three hours. The formulation was reconstituted with 4 mL of pH 5.2 sodium acetate buffer (0.1 M) and mixture vortexed for 30-60 seconds, until a milky white suspension/emulsion was formed. The resulting suspension/emulsion was sonicated in a water bath for ~10-15 minutes at ~30° C. The suspension/emulsion was vortexed gently for 60 seconds immediately prior to filling into hard gelatin capsule (size 11). The contents of the capsule are provided in Table 4.

TABLE 4

Formulation 4.

| Ingredient | Function | mg/dose | % w/w |
|---|---|---|---|
| Captex 1000 (triglyceryl decanoate) | "permeation enhancer" | 203 mg | 3.0% |
| Glyceryl mono decanoate (monoglyceryl decanoate) | permeation enhancer" "P4" | 67 mg | 1.0% |
| Tween 80 | Surfactant/ Emulsifier | 280 mg | 4.2% |
| PEG 400 didecanoate[a] | "permeation enhancer" | 1620 mg | 24.1% |
| Cefepime HCl | Active | *540 mg | 8.0% |
| Buffer, pH 5.2, Na Acetate | Medium | 4.0 mL | 59.6% |

[a]Composition: free capric acid (0.98 w/w %), free PEG 400 (0.1% by HPLC), PEG 400 monodecanoate (0.9% fatty acid ester fraction by HPLC), and PEG 400 didecanoate (99.1% fatty acid ester fraction by HPLC).
b. *as free base The filled capsules were dosed shortly after filling (see Example 7).

EXAMPLE 6

Emulsion Formulation Using a Substantially Pure Diester of PEG 400 and a Taste-Masking Additive A taste-masked formulation of cefepime was prepared. Substantially pure PEG 400 didecanoate, Tween 80, and lemon oil were mixed by vortexing for 30 seconds. To this mixture was added 900 mg of the taste masking blend (Acesulfame K, sucralose, sucrose, and sodium citrate, mixed using a bottle blender (Mini-Blend) for 10 minutes) and 540 mg of cefepime hydrochloride USP, and the resulting mixture was vortexed for an additional 60 seconds. Prior to reconstitution, the formulation was kept at room temperature for a minimum of three hours. The formulation was reconstituted with 2.6 mL of pH 5.2 Sodium Acetate buffer (0.1 M) and mixture vortexed for 30-60 seconds, until a milky white suspension/emulsion was formed. The resulting suspension/emulsion was sonicated in a water bath for ~10-15 minutes at ~30° C. The suspension/emulsion was vortexed gently for 60 seconds immediately prior to filling into hard gelatin capsule (size 11). The contents of the capsule are provided in Table 5.

TABLE 5

Formulation 5.

| Ingredient | Function | mg/dose | % w/w |
|---|---|---|---|
| PEG 400 didecanoate[a] | "permeation enhancer" | 2160 mg | 32.5% |
| Tween 80 | Surfactant/Emulsifier | 324 mg | 4.9% |
| Lemon Oil, Calif. Type | Flavoring agent | 116 mg | 1.7% |
| Acesulfame K | Sweetening agent | 29 mg | 0.4% |
| Sucralose | Sweetening agent | 21 mg | 0.3% |
| Sucrose, crystalline | Sweetening agent/Diluent | 829 mg | 12.5% |
| Sodium citrate, powder | pH modifier | 21 mg | 0.3% |
| Cefepime HCl | Active | *540 mg | 8.1% |
| Na acetate buffer, pH 5.2 | Medium | 2.6 mL | 39.2% |

[a]Composition: free capric acid (0.28 w/w %), free PEG 400 (0.0% by HPLC), PEG 400 monodecanoate (1.14% fatty acid ester fraction by HPLC), and PEG 400 didecanoate (98.8.% fatty acid ester fraction by HPLC).
b. *as free base The filled capsules were dosed shortly after filling (see Example 6).

EXAMPLE 7

Pharmacokinetic Behavior of Formulations 1-5

The objective of this study was to assess the pharmacokinetic profiles of cefepime in different vehicles following single doses administered orally as solutions or suspensions in capsules to male beagle dogs (*Canis familiaris*). Animals selected for use in this study were as uniform in age and weight as possible. Dogs were approximately 7-8 months of age at the initiation of dosing. The weight range for the animals at initial dosing was 9.15 to 10.05 kg. Treatment of the animals was in accordance with regulations outlined in the USDA Animal Welfare Act (9 CFR Parts 1, 2 and 3) and the conditions specified in the Guide for the Care and Use of Laboratory Animals (National Academy Press, Washington D.C., 1996).

Purina Advanced Protocol™ Certified High Density Canine Diet 5L66 was provided daily in amounts appropriate for the size and age of the animals. Feed was offered for approximately one hour each day during the acclimation and the treatment periods. The animals were fasted at least 12 hours prior to each dose and offered feed approximately four hours after dosing. Water was available ad libitum except between one hour prior to and four hours following dosing.

Formulation 1-5 were administered within one hour of preparation.

The animals were fasted at least 12 hours prior to each dose and offered feed after the 4-hour blood sample has been taken. Water was withheld for one hour prior to and four hours following each dosing event. Each dosing evening was followed by a ~50 mL dose of water. Each dosing event was separated by a wash-out period.

Blood was collected from the animals for pharmacokinetic analysis. Approximately 1 mL of blood was collected in $K_3$EDTA tubes via the jugular (or other suitable vein). For each dosing event, blood was collected at 8 time points, as shown in Table 6A.

TABLE 6A

Sample Collection Time points (approximate times).

| Collection Time | Window |
|---|---|
| 15 min | ±1 min |
| 30 min | ±2 min |
| 45 min | ±3 min |
| 1 hr | ±4 min |
| 1.5 hr | ±4 min |
| 2 hr | ±5 min |
| 3 hr | ±10 min |
| 4 hr | ±10 min |

Following blood collection, the samples were kept on ice and centrifuged (within ~30 minutes of collection) under refrigeration (~5° C. for ~10 minutes at ~2000×g). The plasma was harvested into a single tube for each animal at each time point and stored frozen at approximately −70° C. The samples were later thawed and analyzed.

The peak plasma concentration ($C_{max}$), the time required to achieve the peak plasma concentration ($T_{max}$), and the area under the plasma concentration time curve (AUC) was calculated from the plasma concentration data. The plasma terminal half-life ($T_{1/2}$) was estimated if possible. Oral bioavailability was calculated by comparison of the circulating concentrations to those observed for intravenously administered drug. All pharmacokinetic calculations were done using WinNonlin version 4.1 (Pharsight Corp) by non-compartmental analysis. The mean pharmacokinetic parameters are provided in Table 6B.

TABLE 6B

Mean pharmacokinetic parameters.

| Formulation[a] | $T_{1/2}$ (min) | $T_{max}$ (min) | $C_{max}$ (μg/mL) | $AUC_{all}$ (min * μg/mL) | $AUC_{0-\infty}$ (min * μg/mL) | Bioavailability |
|---|---|---|---|---|---|---|
| 1 | 63.8 | 33.8 | 26.1 | 2550 | 2760 | 15.3 ± 5.02% |
| 2 | 74.3 | 41.3 | 33.5 | 3710 | 4140 | 22.2 ± 6.23% |
| 3 | 93.3 | 41.3 | 11.7 | 1530 | 1900 | 9.15 ± 0.84% |
| 4 | 89.6 | 48.8 | 23.1 | 2930 | 3460 | 17.6 ± 5.21% |
| 5 | 63.4 | 71.3 | 38.2 | 4610 | 5250 | 27.6 ± 4.61% |

[a]Oral capsule (50 mg/kg) followed by 50-mL chase with water.
Error: SEM

The results show that (i) PEG fatty acid diesters are more potent enhancers of oral bioavailability than PEG fatty acid monoesters, (ii) a PEG fatty acid diester to drug ratio of 4:1 results in better oral absorption than a ratio of 3:1, and (iii) a simple saccharide (e.g., sucrose) in combination with the PEG fatty acid diester can result in still higher oral bioavailability.

EXAMPLE 8

Pharmacokinetic Behavior of Flavored Formulations Dosed at 85 Mg/Kg (Reconstituted Aqueous Solution) and 120 Mg/Kg (Non-Reconstituted Concentrate) in Dogs Formulations 7a, 7b, and 7c (see Tables 7A, 7B, and 7C) were prepared as described below and the pharmacokinetic profile determined using the methods described in Examples 1-6 in a dose escalation study at 85 mg/kg (reconstituted aqueous solution) and 120 mg/kg (non-reconstituted concentrate).

Preparation of formulation 7a: a taste masking blend was prepared by pre-mixing the accurately weighed amounts of Acesulfame K, Sucralose, Sucrose and Sodium Citrate, anhydrous using a V-blender for 15 minutes. For preparation of the 1 g and 4 g unit dosage, accurately weighed amounts of C10 PEG 400 esters (monoesters and diesters), Tween 80, and Lemon Oil were mixed by vortexing for 30 seconds. To this mixture was added the taste masking blend (2.415 g for 1 g unit dosage and 9.656 g for the 4 g unit dosage) and cefepime hydrochloride USP (by assay). The resulting mixture was vortexed for 60 seconds and homogenized using the IKA Ultra IKA ULTRA-TURRAX® T 25 Digital Homogenizer for 12 minutes at a motor speed of 3 (~13,000 RPM). The container was kept in an ice-water bath (~10° C.) during the homogenization process as excessive heat is generated during the mixing. Flavoring agents were added to the homogenized mixture and the contents were homogenized for additional 3 minutes at a motor speed of 3 (~130,000 RPM). The resulting homogenized mixture is self emulsifying when combined with water.

Preparation of formulation 7b: formulation 7a was kept at room temperature for about 2 3 hours. Sterile water was warmed to 30° C. in a water bath. The formulation was reconstituted with 4 mL (for the 1 g unit dosage) and 15 mL (for the 4 g unit dosage) of warm sterile water. The mixture was stirred using a stainless steel or sterile spatula for ca. 2 minutes and vortexed for ca 5 minutes until a semi-transparent white to off-white hazy solution/emulsion was obtained. Additional vortexing for 2 minutes at ~30° C. was performed as necessary to obtain a semi-transparent white to off-white suspension/emulsion free of gritty, undissolved particles. The suspension/emulsion was vortexed gently for 60 seconds immediately prior to filling into hard gelatin capsule (size 11). The filled capsules were dosed as immediately as possible after filling.

Formulation 7c was prepared as described above for formulation 7b, but was reconstituted with a larger volume of warm sterile water.

TABLE 7A

Formulation 7a, a non-reconstituted concentrate (for 120 mg/kg dose)

| Component | Grams per 4 gram dose | % w/w |
|---|---|---|
| Cefepime HCl | *4.001 | *11.7 |
| PEG 400 didecanoate<sup>a</sup> | 16.006 | 46.6 |
| Tween 80, NF | 2.401 | 7.0 |
| Lemon Oil, Cold Pressed, California Type USP | 0.550 | 1.6 |
| Acesulfame K (Sunnett ® Pharma D) | 1.218 | 3.5 |
| Emprove ® Sucralose Powder NF | 0.716 | 2.1 |
| Compressible Sugar DiPac, NF (Sucrose) | 6.143 | 17.9 |
| Sodium Citrate, anhydrous, NF | 1.579 | 4.6 |
| Strawberries and Cream Flavor, artificial USP | 1.000 | 2.9 |
| Banana flavor, artificial USP | 0.720 | 2.1 |
| Total | 34.334 | 100.0 |

<sup>a</sup>Composition: free capric acid (1.8% w/w), free PEG 400 (0.2% by HPLC), PEG 400 monodecanoate (0.4% fatty acid ester fraction by HPLC), and PEG 400 didecanoate (99.4% fatty acid ester fraction by HPLC).
*equivalent to free base.

TABLE 7B

Formulation 7b, reconstituted in 15 mL water (for 85 mg/kg dose).

| Component | Grams per 4 gram dose | % w/w |
|---|---|---|
| Cefepime HCl | *4.001 | *8.1 |
| PEG 400 Decanoate Esters | 16.006 | 32.4 |
| Tween 80, NF | 2.401 | 4.9 |
| Lemon Oil, Cold Pressed, California Type USP | 0.550 | 1.1 |
| Acesulfame K (Sunnett ® Pharma D) | 1.218 | 2.5 |
| Emprove ® Sucralose Powder NF | 0.716 | 1.5 |
| Compressible Sugar DiPac, NF (Sucrose) | 6.143 | 12.5 |
| Sodium Citrate, anhydrous, NF | 1.579 | 3.2 |
| Strawberries and Cream Flavor, artificial USP | 1.000 | 2.0 |
| Banana flavor, artificial USP | 0.720 | 1.5 |
| Purified Water USP | 15.000 | 30.4 |
| Total | 49.334 | 100.0 | a. Composition: free capric acid (1.8% w/w), free PEG 400 (0.2% by HPLC), PEG 400 monodecanoate (0.04% fatty acid ester fraction by HPLC), and PEG 400 didecanoate (99.94% fatty acid ester fraction by HPLC).
*equivalent to free base.

TABLE 7C

Formulation 7c, reconstituted in 20 mL water (for 50 mg/kg dose).

| Component | Grams per 4 gram dose | % w/w |
|---|---|---|
| Cefepime HCl | *4.001 | *7.4 |
| PEG 400 Decanoate Esters | 16.006 | 29.5 |
| Tween 80, NF | 2.401 | 40.4 |
| Lemon Oil, Cold Pressed, California Type USP | 0.550 | 1.0 |
| Acesulfame K (Sunnett ® Pharma D) | 1.218 | 2.0 |
| Emprove ® Sucralose Powder NF | 0.500 | 0.9 |
| Compressible Sugar DiPac, NF (Sucrose) | 6.143 | 11.3 |
| Sodium Citrate, dihydrate, NF | 1.800 | 3.3 |
| Strawberries and Cream Flavor, artificial USP | 1.000 | 1.8 |
| Banana flavor, artificial USP | 0.720 | 1.3 |
| Purified Water USP | 20.000 | 36.8 |
| Total | 54.334 | 100.0 | a. Composition: free capric acid (0.04% w/w), free PEG 400 (0.0% by HPLC), Other (0.3%) PEG 400 monodecanoate (4.65% fatty acid ester fraction by HPLC), and PEG 400 didecanoate (95.32% fatty acid ester fraction by HPLC).
b. *equivalent to free base.

The mean oral bioavailabilies observed for formulations 7a-7c in beagle dogs are provided in Table 7D.

TABLE 7D

Mean pharmacokinetic parameters.

| Formulation[a] | Dose (mg/kg) | Bioavailability |
|---|---|---|
| 7A | 120 | 19.49% |
| 7B | 85 | 28.09% |
| 7C | 50 | 27.94% |

[a]Oral capsule followed by 50-mL chase with water.

This study demonstrates enhanced oral bioavailability with and without prior reconstitution in water. Absorption enhancement is higher when the formulation is reconstituted in water as an emulsion prior to dosing.

EXAMPLE 9

Comparison of Glyceride Ester Formulations to PEG Ester Formulations

This study was undertaken to assess the relative bioavailability of cefepime in formulations including PEG esters (formulation 8d) and excluding PEG esters (formulations 8a-8c). For each formulation, a quantity of aqueous buffer and cefepime were combined to form a first solution, and a quantity of aqueous buffer, permeation enhancer, and emulsifier were combined to form a second solution. The two solutions were mixed to form an emulsion, placed into a capsule, and orally administered to a dog at a dosing level of 50 mg/kg, followed by a 30 mL chase with water.

TABLE 8A

Formulation 8a.

| Ingredient | Function | mg/dose | % w/w |
|---|---|---|---|
| Glyceryl tri decanoate (triglyceryl decanoate) | permeation enhancer | 630 mg | 7.36% |
| Glyceryl mono decanoate (monoglyceryl decanoate) | permeation enhancer | 420 mg | 4.9% |
| Tween 20 | Emulsifier | 158 mg | 1.85% |
| Buffer, pH 5.2, Na Acetate | Medium | 7.0 mL | 81.8% |
| Cefepime HCl | Active | *350 mg | 4.1% |

*mass of free base

TABLE 8B

Formulation 8b.

| Ingredient | Function | mg/dose | % w/w |
|---|---|---|---|
| Glyceryl tri decanoate (triglyceryl decanoate) | permeation enhancer | 1440 mg | 12.9% |
| Glyceryl mono decanoate (monoglyceryl decanoate) | permeation enhancer | 960 mg | 8.6% |
| Tween 20 | Emulsifier | 361.1 mg | 3.2% |
| Buffer, pH 5.2, Na Acetate | Medium | 8.0 mL | 71.6% |
| Cefepime HCl | Active | *400 mg | 3.6% |

*mass of free base

TABLE 8C

Formulation 8c.

| Ingredient | Function | mg/dose | % w/w |
|---|---|---|---|
| Glyceryl tri decanoate (triglyceryl decanoate) | permeation enhancer | 360 mg | 4.0% |
| Glyceryl mono decanoate (monoglyceryl decanoate) | permeation enhancer | 240 mg | 2.6% |
| Tween 20 | Emulsifier | 90 mg | 1.0% |
| Buffer, pH 5.2, Na Acetate | Medium | 8 mL | 88.0% |
| Cefepime HCl | Active | *400 mg | 4.4% |

*mass of free base

TABLE 8D

Formulation 8d.

| Ingredient | Function | mg/dose | % w/w |
|---|---|---|---|
| Glyceryl tri decanoate (triglyceryl decanoate) | permeation enhancer | 480 mg | 4.55% |
| Glyceryl mono decanoate (monoglyceryl decanoate) | permeation enhancer | 320 mg | 3.0% |
| Tween 20 | Emulsifier | 120 mg | 1.14% |
| PEG 400 decanoate[a] | permeation enhancer | 1600 mg | 15.16% |
| Buffer, pH 5.2, Na Acetate | Medium | 7.5 mL | 71.06% |
| Cefepime HCl | Active | *533.3 mg | 5.05% |

[a]Composition: free capric acid (0.3% w/w), free PEG 400 (2.7% by HPLC), PEG 400 monodecanoate (35% fatty acid ester fraction by HPLC), and PEG 400 didecanoate (62.3% fatty acid ester fraction by HPLC).
*as free base The results of the dog study are provided in Table 8E. The inclusion of PEG esters (formulation 8d) results in a much higher oral bioavailability for cefepime in comparisons to formulations lacking PEG esters (formulations 8a-8c).

TABLE 8E

| Formulation | $T_{1/2}$ (min) | $T_{max}$ (min) | $C_{max}$ (μg/mL) | $AUC_{all}$ (min * μg/mL) | $AUC_{0-\infty}$ (min * μg/mL) | Bioavailability |
|---|---|---|---|---|---|---|
| 8a | 75.5 | 37.5 | 9.60 | 1350 | 1590 | 8.10 ± 0.78% |
| 8b | 76.9 | 41.3 | 13.5 | 1830 | 1970 | 11.0 ± 0.92% |
| 8c | 104 | 30.0 | 10.7 | 1340 | 1750 | 8.01 ± 1.19% |
| 8d | 92.5 | 56.3 | 26.9 | 3930 | 4890 | 23.6 ± 4.34% |

Error = SEM

EXAMPLE 10

Comparison of a Labrasol Formulation to a PEG Ester Formulation

This study was undertaken to compare the relative bioavailability of cefepime in formulations including labrasol (formulation 9a) and PEG esters (formulations 9b). Each formulation was placed into a capsule, and orally administered to a dog at a dosing level of 50 mg/kg, followed by a 50 mL chase with water.

TABLE 9A

Formulation 9a.

| Ingredient | Function | mg/dose | % w/w |
|---|---|---|---|
| Labrasol, USP/EUP | permeation enhancer | 7200 mg | 48.7% |
| Na Citrate, dihydrate | pH modifying agent | 328 mg | 2.2% |
| Na Chloride | isotonic agent | 48 mg | 0.3% |
| Cefepime HCl | Active | *1200 mg | 8.1% |
| Buffer (NaAC, 0.1M, pH 5.2) | Medium | 6 mL | 40.6% |

*as free base

TABLE 9B

Formulation 9b.

| Ingredient | Function | mg/dose | % w/w |
|---|---|---|---|
| PEG 400 decanoate[a] | permeation enhancer | 2000 mg | 32.8% |
| Tween 80 | Emulsifier | 300 mg | 4.9% |
| Cefepime HCl | Active | *500 mg | 8.2% |
| Buffer, pH 5.2, Na Acetate | Medium | 3.3 mL | 54.1% |

[a]Composition: free capric acid (0.3% w/w), free PEG 400 (2.7% by HPLC), PEG 400 monodecanoate (35% fatty acid ester fraction by HPLC), and PEG 400 didecanoate (62.3% fatty acid ester fraction by HPLC).
*as free base The results of the dog study are provided in Table 9C. The AUC data show that PEG esters at a 1:4 ratio of drug to PEG ester (formulation 9b) results in a much higher oral bioavailability for cefepime in comparisons to formulations containing a 1:6 ratio of drug to labrasol (formulation 9a).

TABLE 9C

| Formulation | $T_{1/2}$ (min) | $T_{max}$ (min) | $C_{max}$ (μg/mL) | $AUC_{all}$ (min * μg/mL) | $AUC_{0-\infty}$ (min * μg/mL) |
|---|---|---|---|---|---|
| 9a | 56.7 | 48.8 | 24.2 | 2560 | 2750 |
| 9b | 69.4 | 50.0 | 36.4 | 4270 | 4860 |

EXAMPLE 11

Cefepime Formulation for Reconstitution

A Formulation for reconstitution can contain 1.0 g (see Table 11) or 4.0 g cefepime in each 8.58 and 34.34 grams of suspension for reconstitution. The formulation can be provided in two prepackaged units, one container containing cefepime active pharmaceutical ingredient (i.e., the cefepime container) and a second container containing concentrated diluents (i.e., the concentrated diluents container containing PEG 400 Decanoate Esters, Tween 80, sucrose, flavorings, and buffers).

TABLE 11

| Component | Grams per 1 gram dose | % w/w |
|---|---|---|
| Cefepime HCl[a] | *1.000 | *7.9 |
| PEG 400 Decanoate Esters | 4.002 | 31.8 |
| Tween 80, NF | 0.600 | 4.8 |
| Lemon Oil, Cold Pressed, California Type USP | 0.138 | 1.1 |
| Acesulfame K (Sunnett ® Pharma D) | 0.305 | 2.4 |
| Emprove ® Sucralose Powder NF | 0.179 | 1.4 |
| Compressible Sugar DiPac, NF (Sucrose) | 1.536 | 12.2 |
| Sodium Citrate, dihydrate, NF | 0.395 | 3.1 |
| Strawberries and Cream Flavor, artificial USP | 0.250 | 2.0 |
| Banana flavor, artificial USP | 0.180 | 1.4 |
| Purified Water USP | 4.000 | 31.8 |
| Total | 12.584 | 100.0 |

[a]*= equivalent to free base.

First, the contents of the cefepime container and the concentrated diluents container are mixed, followed by the addition of ca. 4 mL of water. The mixture is stirred until a semi-transparent white to off-white suspension/emulsion is formed. The emulsion is then immediately administered to a subject.

Other Embodiments

All publications, patent applications, and patents mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

This application claims benefit of the U.S. Provisional Application No. 61/549,882, filed Oct. 21, 2011, and incorporated herein by reference.

Other embodiments are within the claims.

The invention claimed is:

1. A pharmaceutical composition in oral dosage form comprising:
 a) a drug; and
 b) an additive comprising from 10% to 80% (w/w) of a PEG fatty acid diester and from 0.5% to 20% (w/w) of a saccharide,
 wherein the ratio by weight of said PEG fatty acid diester to said drug is greater than 1:1 and said additive is present in an amount sufficient to increase the oral bioavailability of said drug.

2. The pharmaceutical composition of claim 1, wherein said pharmaceutical composition comprises from 40% to 75% (w/w) of said PEG fatty acid diester.

3. The pharmaceutical composition of claim 2, wherein the ratio by weight of said PEG fatty acid diester to said drug is greater than 3.0:1.

4. The pharmaceutical composition of claim 1, wherein said PEG fatty acid diester is the decanoate diester of a polyethylene glycol having from 1 to 20 PEG units.

5. The pharmaceutical composition of claim 4, wherein said PEG fatty acid diester is the decanoate diester formed from a polyethylene glycol mixture having an average chain length of from 8 to 9 PEG units in length.

6. The pharmaceutical composition of claim 1, wherein said saccharide is selected from sucrose and fructose.

7. The pharmaceutical composition of claim 1, wherein said drug is a β-lactam antibiotic selected from cephalosporins, carbapenems, monobactams, penicillins, penems, carbacephems, and oxacephems.

8. The pharmaceutical composition of claim 7, wherein said drug is a cephalosporin, or a salt thereof.

9. The pharmaceutical composition of claim 8, wherein said cephalosporin, or a salt thereof, is positively charged.

10. The pharmaceutical composition of claim 8, wherein said drug is a cephalosporin, or a salt thereof, selected from cefepime, cefalonium, cephaloridine, cefpimizole, ceftazidime, cefluprenam, cefozopran, cefpirome, cefquinome, cefmepidium, ceftaroline, ceftaroline fosamil, and salts thereof.

11. The pharmaceutical composition of claim 10, wherein said cephalosporin, or a salt thereof, is cefepime, or a salt thereof.

12. The pharmaceutical composition of claim 7, wherein said drug is a carbapenem, or a salt thereof.

13. The pharmaceutical composition of claim 12, wherein said carbapenem, or a salt thereof, is meropenem, ertapenem, or doripenem, or a salt thereof.

14. A method of treating a bacterial infection in a subject, said method comprising orally administering to said subject a pharmaceutical composition of claim 7, wherein said composition is administered in an amount effective to treat said infection.

15. The method of claim 14, wherein said drug is cefepime and said infection is selected from febrile neutropenia and uncomplicated or complicated urinary tract infection.

16. The pharmaceutical composition of claim 1 in oral dosage form comprising:
   a) cefepime, or a pharmaceutically acceptable salt thereof; and
   b) an additive comprising from 10% to 80% (w/w) of a PEG fatty acid diester and from 0.5% to 20% (w/w) of a saccharide,
   wherein said additive is present in an amount sufficient to increase the oral bioavailability of said drug and wherein the ratio by weight of said additive to said cefepime is greater than 1:1.

17. The pharmaceutical composition of claim 16, wherein said pharmaceutical composition comprises from 40% to 75% (w/w) of said PEG fatty acid diester.

18. The pharmaceutical composition of claim 16, wherein said pharmaceutical composition is in a unit dosage form comprising from 250 milligrams to 5.0 grams of cefepime, or a pharmaceutically acceptable salt thereof.

19. The pharmaceutical composition of claim 16, wherein said saccharide is selected from sucrose and fructose.

20. A reconstitutable pharmaceutical composition comprising from 0.5% to 20% (w/w) of a drug; and from 40% to 80% (w/w) of an additive comprising from 10% to 80% (w/w) of a PEG fatty acid diester and from 0.5% to 20% (w/w) of a saccharide,
   wherein the ratio by weight of said PEG fatty acid diester to said drug is greater than 1:1 and said additive is present in an amount sufficient to increase the oral bioavailability of said drug.

21. The reconstitutable pharmaceutical composition of claim 20, wherein the ratio by weight of said PEG fatty acid diester to said drug is greater than 3.0:1.

22. The reconstitutable pharmaceutical composition of claim 20, wherein said PEG fatty acid diester is the decanoate diester of a polyethylene glycol having from 1 to 20 PEG units.

23. The reconstitutable pharmaceutical composition of claim 22, wherein said PEG fatty acid diester is the decanoate diester formed from a polyethylene glycol mixture having an average chain length of from 8 to 9 PEG units in length.

24. The reconstitutable pharmaceutical composition of claim 20, wherein said reconstitutable pharmaceutical composition is a liquid concentrate that can form an emulsion when mixed with an aqueous liquid.

25. The reconstitutable pharmaceutical composition of claim 24, wherein said composition is a self emulsifying composition.

26. The reconstitutable pharmaceutical composition of claim 20, wherein said reconstitutable pharmaceutical composition is a solid or solid matrix that can be mixed with water.

27. The reconstitutable pharmaceutical composition of claim 26, wherein said composition is a self emulsifying composition.

28. The reconstitutable pharmaceutical composition of claim 27, wherein said composition is formulated in unit dosage form for oral administration as a hard gel capsule, soft gel capsule, effervescent tablet, or as a sprinkle.

29. The reconstitutable pharmaceutical composition of claim 20, wherein said saccharide is selected from sucrose and fructose.

30. The reconstitutable pharmaceutical composition of claim 20, wherein said drug is a β-lactam antibiotic selected from cephalosporins, carbapenems, monobactams, penicillins, penems, carbacephems, and oxacephems.

31. The reconstitutable pharmaceutical composition of claim 30, wherein said drug is a cephalosporin, or a salt thereof.

32. The reconstitutable pharmaceutical composition of claim 31, wherein said cephalosporin, or a salt thereof, is cefepime, or a salt thereof.

33. The reconstitutable pharmaceutical composition of claim 30, wherein said drug is a carbapenem, or a salt thereof.

34. The reconstitutable pharmaceutical composition of claim 33, wherein said carbapenem, or a salt thereof, is meropenem, ertapenem, or doripenem, a salt thereof.

35. A kit comprising:
   a) a first container comprising a drug;
   b) a second container comprising an additive comprising from 10% to 80% (w/w) of a PEG fatty acid diester and from 0.5% to 20% (w/w) of a saccharide; and
   c) instructions for mixing the contents of said first container with the contents of said second container.

36. The kit of claim 35, wherein said saccharide is selected from sucrose and fructose.

37. The kit of claim 35, wherein said drug is a 3-lactam antibiotic selected from cephalosporins, carbapenems, monobactams, penicillins, penems, carbacephems, and oxacephems.

38. The kit of claim 37, wherein said drug is a cephalosporin, or a salt thereof.

39. The kit of claim 38, wherein said cephalosporin, or a salt thereof, is cefepime, or a salt thereof.

40. The kit of claim 37, wherein said drug is a carbapenem, or a salt thereof.

41. The kit of claim 40, wherein said carbapenem, or a salt thereof, is meropenem, ertapenem, or doripenem, or a salt thereof.

42. A composition comprising from 10% to 80% (w/w) of a PEG fatty acid diester and from 5% to 40% (w/w) of a saccharide.

43. The composition of claim 42, wherein said saccharide is selected from sucrose and fructose.

* * * * *